United States Patent
Danino et al.

(10) Patent No.: US 8,865,222 B2
(45) Date of Patent: *Oct. 21, 2014

(54) BETA-CASEIN ASSEMBLIES FOR ENRICHMENT OF FOOD AND BEVERAGES AND METHODS OF PREPARATION THEREOF

(75) Inventors: Dganit Danino, Nesher (IL); Yoav D. Livney, Misgav (IL); Ory Ramon, Kibbutz Sarid (IL); Irina Portnoy, Nesher (IL); Uri Cogan, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 366 days.

This patent is subject to a terminal disclaimer.

(21) Appl. No.: 12/867,204

(22) PCT Filed: Feb. 11, 2009

(86) PCT No.: PCT/IL2009/000154
§ 371 (c)(1),
(2), (4) Date: Nov. 1, 2010

(87) PCT Pub. No.: WO2009/101612
PCT Pub. Date: Aug. 20, 2009

(65) Prior Publication Data
US 2011/0038987 A1    Feb. 17, 2011

Related U.S. Application Data

(60) Provisional application No. 61/027,633, filed on Feb. 11, 2008.

(51) Int. Cl.
| | | |
|---|---|---|
| A61K 9/14 | (2006.01) | |
| A61K 9/16 | (2006.01) | |
| A61K 9/50 | (2006.01) | |
| A23L 1/305 | (2006.01) | |
| A23J 1/22 | (2006.01) | |
| A23B 4/03 | (2006.01) | |
| A61K 31/665 | (2006.01) | |
| A61K 31/415 | (2006.01) | |
| A61K 9/00 | (2006.01) | |
| A61K 9/107 | (2006.01) | |
| A61K 31/573 | (2006.01) | |

(52) U.S. Cl.
CPC ................. *A61K 9/00* (2013.01); *A61K 9/1075* (2013.01); *A61K 31/415* (2013.01); *A61K 31/573* (2013.01)
USPC ............. 424/499; 424/489; 426/72; 426/657; 514/100; 514/141; 514/403

(58) Field of Classification Search
None
See application file for complete search history.

(56) References Cited

U.S. PATENT DOCUMENTS

| | | |
|---|---|---|
| 5,173,322 A | 12/1992 | Melachouris |
| 5,318,793 A | 6/1994 | Melachouris |
| 5,399,363 A | 3/1995 | Liversidge |
| 5,405,756 A | 4/1995 | Naito |
| 5,603,930 A | 2/1997 | Brassart |
| 5,833,953 A | 11/1998 | Berrocal |
| 6,290,974 B1 | 9/2001 | Swaisgood |
| 6,503,545 B1 | 1/2003 | Perlman |
| 6,652,875 B1 | 11/2003 | Bannister |
| 6,991,823 B2 | 1/2006 | Augustin |
| 2002/0054914 A1 | 5/2002 | Morcol |
| 2003/0180367 A1 | 9/2003 | Parikh |
| 2004/0137071 A1 | 7/2004 | Unger |
| 2004/0234666 A1* | 11/2004 | Law et al. .................... 426/580 |
| 2005/0031544 A1 | 2/2005 | Njemanze |
| 2007/0104847 A1* | 5/2007 | O'Mahony et al. .......... 426/582 |
| 2007/0166368 A1 | 7/2007 | Singh |
| 2008/0145432 A1 | 6/2008 | Kakizawa |
| 2009/0029017 A1 | 1/2009 | Singh |
| 2010/0062073 A1 | 3/2010 | Beyerinck |
| 2011/0052703 A1* | 3/2011 | Barenholz et al. ............ 424/489 |
| 2012/0070469 A1 | 3/2012 | Barenholz |

FOREIGN PATENT DOCUMENTS

| | | |
|---|---|---|
| EP | 1348430 | 10/2003 |
| GB | 2041378 | 9/1980 |
| WO | 96/29340 | 9/1996 |
| WO | 00/06108 | 2/2000 |
| WO | 02/064112 | 8/2002 |
| WO | 2004/000252 | 12/2003 |
| WO | 2007/017513 | 2/2007 |

(Continued)

OTHER PUBLICATIONS

Aoki, T. et al., (1989) Incorporation of individual casein constituents into micelles in artificial casein micelles. Nippon Chikusan Gakkaiho 60:583-589.

(Continued)

*Primary Examiner* — Jeffrey T Palenik
(74) *Attorney, Agent, or Firm* — Browdy and Neimark, PLLC

(57) ABSTRACT

The invention relates to a composition for the enrichment of food and/or beverage and to a method of preparing such composition. The composition comprises additive loaded beta-casein micelles which are of a diameter of about 100 nm or less. These nano-sized beta-casein assemblies are formed at pH values which are preferably one or more pH units above or below the pI of the protein (pI=5.3). More preferably the beta-casein nano-assemblies are formed at a pH range between about 6.0 and about 8, or between about 2.0 and about 4.2. The invention provides vehicles for delivery of additives via transparent beverages and other foods and drinks and/or acidic foods and drinks and/or non fat foods and drinks.

18 Claims, 20 Drawing Sheets

(56) References Cited

FOREIGN PATENT DOCUMENTS

| | | |
|---|---|---|
| WO | 2007/069272 | 6/2007 |
| WO | 2007/122613 | 11/2007 |
| WO | WO 2007122613 A1 * | 11/2007 |
| WO | 2008/135852 | 11/2008 |
| WO | 2009/101612 | 8/2009 |
| WO | 2009/101614 | 8/2009 |

OTHER PUBLICATIONS

Bellare, J. R. et al., (1988), Controlled environment vitrification system: an improved sample preparation technique. Electron Microsc. Technique 10:87-111.

Bootz, Alexander et al., (2004) Comparison of scanning electron microscopy, dynamic light scattering and analytical ultracentrifugation for the sizing of poly(butyl cyanoacrylate) nanoparticles. Eur J Pharm Biopharm 57(2):369-375.

Brophy, Brigid et al., (2003) Cloned transgenic cattle produce milk with higher levels of beta-casein and kappa-casein. Nat Biotechnol 21(2):157-162.

Christiaens, Bart et al., (2002), Tryptophan fluorescence study of the interaction of penetratin peptides with model membranes. Eur J Biochem 269(12):2918-2926.

Farrell, H. M. Jr. et al., (2006), Casein micelle structure: What can be learned from milk synthesis and structural biology?. Current Opinion in Colloid and Interface Science 11:135-147.

Forrest, Stephanie A. et al., (2005) Interactions of vitamin D3 with bovine beta-lactoglobulin A and beta-casein. J Agric Food Chem 53(20):8003-8009.

Fornier, Monica N. et al., (2007) Increased dose density is feasible: a pilot study of adjuvant epirubicin and cyclophosphamide followed by paclitaxel, at 10- or 11-day intervals with filgrastim support in women with breast cancer. Clin Cancer Res 13(1):223-227.

Hogan, Sean A. et al., (2001) Microencapsulating Properties of Sodium Caseinate. Journal of Agricultural and Food Chemistry 49:1934-1938.

Horne, David S. (2002) Casein structure, self-assembly and gelation. Current Opinion in Colloid & Interface Science 7(5-6):456-461.

Jubeh, Tareq Taha at al., (2004) Differential adhesion of normal and inflamed rat colonic mucosa by charged liposomes. Pharm Res 21:447-453.

Jubeh, Tareq Taha et al., (2005) Local prevention of oxidative stress in the intestinal epithelium of the rat by adhesive liposomes of superoxide dismutase and tempamine. Mol Pharm 2(1):2-11.

Jubeh, Tareq Taha et al.,(2006) Local treatment of experimental colitis in the rat by negatively charged liposomes of catalase, TMN and SOD. J Drug Target 14(3)155-163.

Kauf, M. C. W. and Kensinger, R. S. (2002) Purification of porcine beta-casein, N-terminal sequence, quantification in mastitic milk. J Anim Sci 80:1863-1870.

Knepp, W. A. et al', (1993) Synthesis, properties, and intratumoral evaluation of mitoxantrone-loaded casein microspheres in Lewis lung carcinoma. J Pharm Pharmacol 45(10):887-891.

Knoop, Anne Marie et al., (1979) Sub-structure of synthetic casein micelles. Journal of Dairy Research 46:347-350.

Le Graet, Y. And Brule, G. (1993) Effects of pH and ionic strength on distribution of mineral salts in milk. Lait 73:51-60 article in French with summary in English.

Le Graet, Y. et al., (1999) pH-induced solubilization of minerals from casein micelles: influence of casein concentration and ionic strength. J Dairy Res 66:215-224.

Mattila, Pirjo et al., (2001), Contents of vitamins, mineral elements, and some phenolic compounds in cultivated mushrooms. Journal of agricultural and food chemistry 49:2343-2348.

O'Connell, J. et al.,(2003) Association behavior of beta-casein. Journal of Colloid and Interface Science 258(1): 33-39.

Pan, X. et al., (2007) Simultaneous nanoparticle formation and encapsulation driven by hydrophobic interaction of casein-graft-dextran and beta-carotene. Journal of Colloid and Interface Science 315(2):456-463.

Portnaya, I. et al., (2006) Micellization of bovine beta-casein studied by isothermal titration microcalorimetry and cryogenic transmission electron microscopy. J Agric Food Chem 54(15):5555-5561.

Portnaya, I. et al., (2008) Self-assembly of bovine beta-casein below the isoelectric Ph. J Agric Food Chem 56 (6):2192-2198.

Renken, Shelly a. And Warthesen, Joseph J. (1993) Vitamin D stability in milk. J Food Science 58(3):552-556.

Ribadeau Dumas, Bruno et al., (1972) Primary structure of bovine beta casein. Complete sequence. Eur J Biochem 25(3):505-514 article in French with English summary.

Semo, Efrat et al., (2007) Casein micelle as a natural nano-capsular vehicle for nutraceuticals. Food Hydrocolloids 21 (5-6):936-942.

Tirosh, Boaz et al., (2009) Transferrin as a luminal target for negatively charged liposomes in the inflamed colonic mucosa. Mol Pharm 6(4):1083-1091.

Weissenboeck, Andrea et al., (2004) Binding and Uptake of Wheat Germ Agglutinin-Grafted PLGA-Nanospheres by Caco-2 Monolayers. Pharm Res 21(10)1917-1923.

Zhang, Liangke et al. (2004) Uptake of folate-conjugated albumin nanoparticles to the SKOV3 cells. Int J Pharm 287 (1-2):155-162.

Zhang, X. et al., (2005) Chaperone-like activity of beta-casein. Int J Biochem Cell Biol 37(6):1232-1240.

Database Biosis [Online] Biosciences informaiotn service, Philadelphia, PA, US; 1979, Evans, M. T. et al., The conformation and aggregation of bovine β-casein A. II. Thermodynamics of thermal association and the effects of changes in polar and apolar interactions on micellization, XP002531439 Database accession No. PREV197968060329 abstract & Biopolymers 1979;18(5):1123-1140.

ISR of NP of PCT/IL09/00154 mailed Oct. 15, 2009.
ISR of PCT/IL2007/000496 mailed Aug. 9, 2007.
ISR of PCT/IL2009/000156 mailed Jul. 10, 2009.
ISR of PCT/IL2009/000155 mailed Jul. 22, 2009.
U.S. Appl. No. 12/297,424, Non-Final Rejection dated May 13, 2011.
U.S. Appl. No. 12/297,424, Final Rejection dated Sep. 23, 2011.
U.S. Appl. No. 12/867,219, Non-Final Rejection Jan. 5, 2012.
U.S. Appl. No. 12/867,219, Final Rejection Sep. 26, 2012.
U.S. Appl. No. 12/867,215, Requirement for Restriction/Election Feb. 1, 2012.
U.S. Appl. No. 12/867,215, Non-Final Rejection May 31, 2012.
Home DS., Casein Interactions: Casting Light on the Black Boxes, the Structure in Dairy Products. Int Dairy 1998;8 (3):171-7.
Karlsson et al., Observations of casein micelles in skim milk concentrate by transmission electron microscopy. LWT—Food Science and Technology 2007; 40(6):1102-7.
Livney D., Experimental report: Comparison of the binding of vitamin D to casein under the conditions of D1 and under the conditions of Livney & Dalgleish, measured by spectrofluorometry.
Thomsen et al., (1995) Solid-state magic-angle spinning 31P-NMR studies of native casein micelles. Eur J Biochem 230: 454-459.
Cogan et al., Binding Affinities of Retinol and Related Compounds to Retinol Binding Proteins, Eur. J. Biochem. 65:71-78 (1976).
Dalgleish and Law, Sodium caseinates—composition and properties of different preparations. International Journal of Dairy Technology 41(1): 1-4 (1988).
Guo et al., Casein precipitation equilibria in the presence of calcium ions and phosphates. Colloids and Surfaces B: Biointerfaces 29: 297-307 (2003).

* cited by examiner

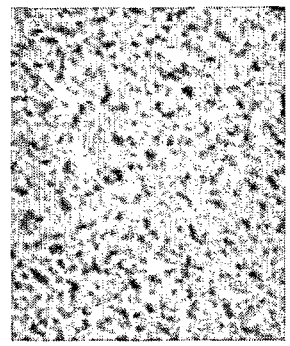 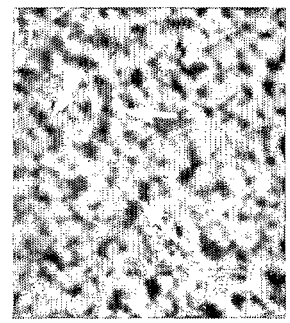
FIG. 2E  FIG. 2F

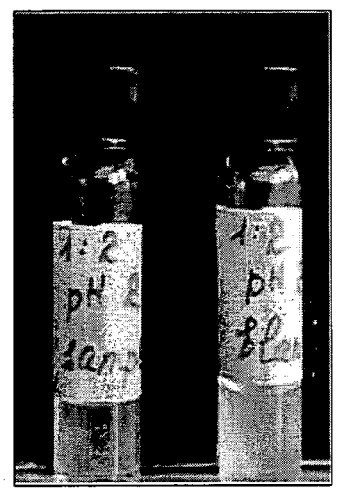
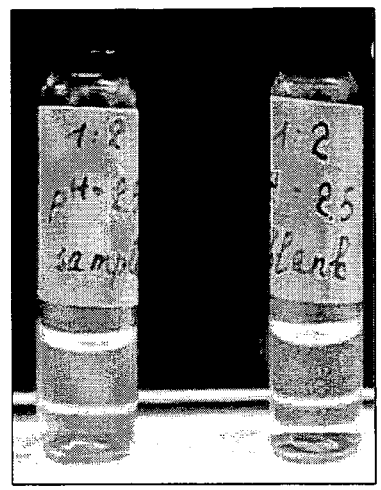
FIG.18A          FIG.18B
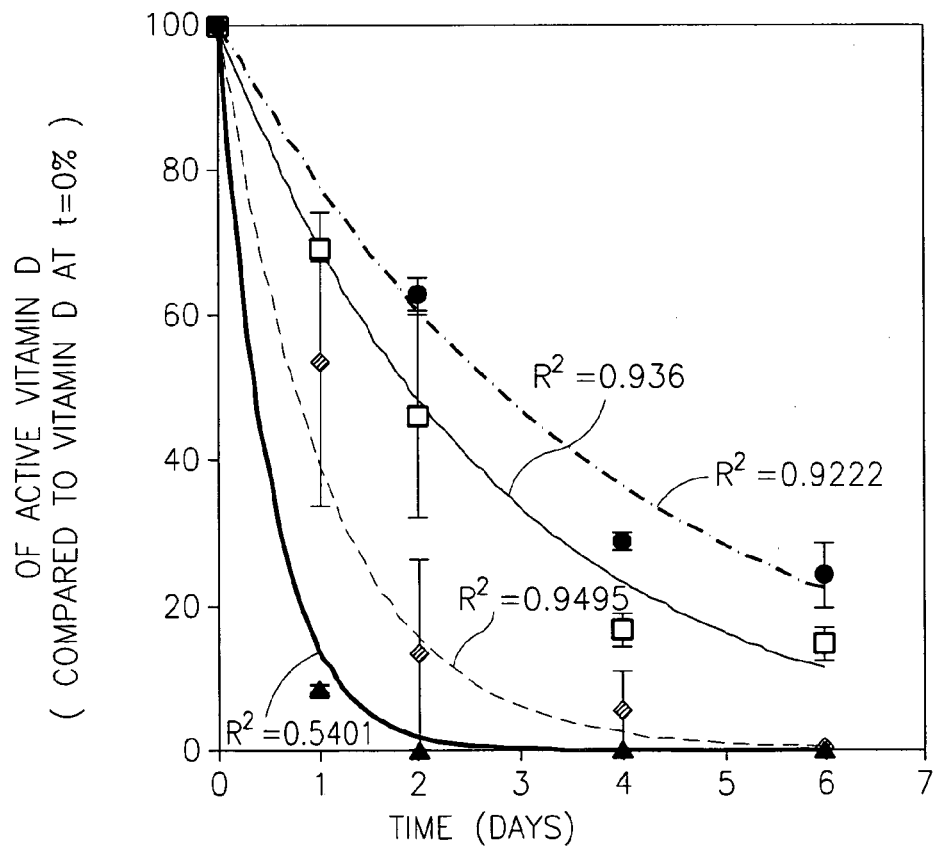
FIG.19

BETA-CASEIN ASSEMBLIES FOR ENRICHMENT OF FOOD AND BEVERAGES AND METHODS OF PREPARATION THEREOF

FIELD OF THE INVENTION

The present invention relates to the field of food technology and delivery of hydrophobic nutraceuticals or additives via beverages and food. In particular, the present invention provides beta-casein micelle assemblies useful for nanoencapsulation, stabilization and protection of hydrophobic additives at a wide range of pH and temperatures. The invention further provides methods of producing same.

BACKGROUND OF THE INVENTION

Functional foods and beverages typically have a health-promoting and/or disease-preventing property beyond their basic supply of nutrients. Functional foods and beverages have been developed by adding to these foods and beverages nutritional supplements, such as vitamins, antioxidants, and other nutraceuticals, which are generally intended to supplement the diet such that it becomes more nutritionally complete, and serve to prevent diseases. Other additives such as aroma compounds, flavors, dyes, and the like, may also be incorporated into foods and beverages.

However, solutions aimed at incorporating nutraceuticals and other additives in foods and beverages, particularly clear ones, at the nano-scale, are still very scarce. Incorporating additives into foods and beverages is still a major challenge in creating advanced functional foods. The challenges are especially great in acidic food products (pH around 2.0-4.2), and in nonfat and low fat foods. The main difficulties are encountered in dispersing, solubilizing, stabilizing and protecting the additives which are often sensitive bioactive compounds.

Further challenges are encountered when trying to add mainly, but not only, water insoluble additives, without compromising sensory properties of the food product. Moreover, stability and preservation of bioactivity need to be maintained throughout product shelf-life.

Maintaining transparency of clear beverages during enrichment is especially challenging, as it further requires the nutraceutical-loaded carrier to be small enough so as not to scatter light and be detected by the naked eye. Furthermore, any matrix containing bioactive ingredients within food or drink needs to be made of food-grade, GRAS (generally recognized as safe) materials and it is desirable that these materials be easily digestible to promote bioavailability and functionality of the bioactive additives. Lastly, a major difficulty arises from the fact that consumers prefer the product to be composed of natural ingredients only. Existing solutions include Gum Arabic-based emulsions, lipid-based systems such as microemulsions, cubosomes and hexosomes, and reformed casein micelles. Gum Arabic (GA) has been extensively used as an emulsifier and stabilizer in beverages, mainly for emulsifying aroma oils in acid drinks. It has good emulsifying and stabilizing capacities, and is considered a natural encapsulator for water-insoluble compounds, such as flavors and nutraceuticals such as lycopene, linoleic acid, and conjugated linoleic acid. GA may provide a reasonable solution in some conditions, but it is very expensive. It is also less stable at low pH conditions (e.g., pH 2.5), than at higher pH values, and it is very variable in composition. Previous experiments performed by some of the inventors showed that GA is a poor barrier to oxygen. Thus nutraceticals sensitive to oxidative stress such omega 3 and 6 fatty acids, PUFA, and oils had a very poor stability when encapsulated in GA (Dror-Katz, MSc thesis, Biotechnology and Food Engineering Dept., Technion, Israel Institute of Technology, 1995)

Lipid-based cubosomes and hexosomes are designed to give solutions for neutral pH conditions, but they are still in research stages. Additionally, these nano-vehicles are relatively large (hundreds of nanometers), thus, their dispersions are not transparent.

Microemulsions prepared from combinations of low molecular weight surfactants (e.g., Brij 96v and Tween 60), limonene and ethanol are another possible solution. However, existing microemulsions are not made of "all natural ingredients".

Certain casein micelles are known in the art. Casein, which accounts for about 80% of milk protein, is naturally organized in micelles. Casein micelles (CM) are designed by nature to efficiently concentrate, stabilize and transport essential nutrients, mainly calcium and protein, for the neonate.

Naturally occurring micelles are spherical colloids, 50-500 nm in diameter (average of 150 nm), made of the main four caseins: $\alpha s1$-casein ($\alpha s1$-CN), $\alpha s2$-CN, $\beta$-CN, and $\kappa$-CN (molar ratio ~4:1:4:1 respectively). The caseins are held together in the micelle by hydrophobic interactions and by bridging of calcium-phosphate nanoclusters bound to serine-phosphate residues present within the casein molecules.

The structure of the casein micelles is important for their biological activity, for their stability and for providing good digestibility of the nutrients comprising the micelles. Harnessing the remarkable casein micelles natural nano-capsules for nano-encapsulation and stabilization of hydrophobic nutraceutical substances was suggested in the prior art. Semo et al., referred to the incorporation of such CM nano-capsules in dairy products without modifying their sensory properties (Semo E. *Food Hydrocolloids* 2007, 21; 936-42, and publication WO/2007/122613) and further suggested their use as delivery agents of sensitive health-promoting substances using natural GRAS (generally regarded as safe) ingredients.

U.S. Pat. No. 6,652,875 provides a formulation for the delivery of bioactive agents to biological surfaces comprising at least one isolated and purified casein protein or salt thereof in water. That disclosure relates to particular isolated and purified casein phosphoproteins in the form of casein calcium phosphate complexes intended to remain on the surface of oral cavity tissues or the gastrointestinal tract. There is neither teaching, nor suggestion regarding formation of nanoparticles, nor introduction of the bioactive compounds into nanoparticles. Furthermore the micelles comprise a casein protein selected from alpha-casein, beta-casein, kappa-casein, and mixtures thereof. This disclosure emphasizes the presence of divalent and trivalent metal ions.

U.S. Patent Application Publication No. 2002/0054914 teaches a calcium phosphate/drug core with casein micelles reconstructed as aggregates around the cores, forming micellar structures, for the delivery of pharmaceutical agents. According to that disclosure, casein molecules are arranged, presumably as micelles, around calcium phosphate particles containing the active drug, and are linked to the therapeutic agent-containing microparticles by mainly calcium phosphate and electrostatic bond interactions.

U.S. Patent Application Publication No. 2009/0029017 provides a protective system for lipids sensitive to oxidative processes by encapsulating them in a complex of casein and whey proteins. The emulsion is reported to stabilize the oxidizable lipid by decreasing its rate of oxidation. The emulsion is further reported to be heat stable which allows it to be heat treated and sterilized. However, the emulsion clearly requires a combination of both types of proteins; furthermore, the effect of low pH values and/or low temperature is not discussed. In fact, the pH is stated to be preferably between 6 and 9, with the upper end of the range even more preferred. Also the complex is stated to be formed by heating to between 70-100 degrees C.

Casein bound to a dextran copolymer nanoparticles encapsulating insoluble β-carotene were disclosed by Pan X. et al. (Journal of Colloid and Interface Science, 2007, 315; 456-63). The nanoparticles formed contained a casein and β-carotene core surrounded by a dextran shell. The particles were shown to have spherical shape and are stable in aqueous solution against dilution, pH change, ionic strength change, $FeCl_3$ oxidation and long term storage. The casein-dextran nanoparticles were suggested as possible delivery agents for unstable and hydrophobic nutrients and drugs. However this disclosure requires the dextran copolymer for forming the nanoparticles.

In some cases caseinates have been used as microencapsulation wall materials. However, caseins forming such artificial capsules have lost the original micellar structure, and the generally larger size of caseinate microcapsules is more likely to impair product smoothness and clearness.

Casein micelles can be re-assembled in vitro, by simulating their formation in the Golgi system of the mammary gland. Reformed casein micelles may be used to encapsulate and protect hydrophobic nutraceuticals, however micelles are not reformed or able to remain stable at an acid pH.

U.S. Pat. No. 5,405,756 discloses acid soluble casein phosphopeptides prepared by enzymatic digestion of intact casein followed by step wise acidification of the digest causing precipitation of acid insoluble molecules. This procedure teaches that caseins tend to precipitate at pH values around the pI of the protein.

WO 2007/122613 described a system based on re-assembled casein micelles for the delivery of hydrophobic biologically active compounds in food and beverages. The invention relates specifically to the incorporation of such re-assembled casein micelles into low-fat or non-fat dairy products or other food or beverage products without adversely modifying their properties. The micelles of the invention are composed of sodium caseinate comprising at least the main four casein proteins and are re-assembled at neutral pH.

Thus, at present, there are only partial solutions to the problems listed above. There currently exists no solution having all of the desired attributes.

SUMMARY OF THE INVENTION

The present invention provides beta-casein micelles or self assemblies as nano-encapsulators for hydrophobic additives. The present invention departs from known casein micelles based delivery vehicles in their exceptional stability at a wide pH range including low pH and at a wide range of temperatures. Nano-assemblies according to embodiments of the invention are small enough so as not to compromise the transparency of clear beverages and the appearance of foods which incorporate them. Thus, the present invention provides vehicles for such challenging delivery tasks, as via transparent beverages and other foods and drinks, for example, clear, nonfat acid beverages and acidic-milk products.

The present invention thus provides for the first time a system based on beta-casein micelles for the delivery of hydrophobic additives at pH as low as 2.0.

The present invention discloses for the first time the formation of stable nanoparticulate β-casein assemblies, which are stable at low pH values, contrary to the teachings of the background art. According to the invention the beta casein micelles are formed preferably one or more pH units above or below the pI of the protein. According to particular embodiments the β-casein nano-assemblies are formed at low pH, optionally and preferably at least two pH units below the pI of beta casein (pI=5.3). However it is within the scope of the present invention that the nano-assemblies may then optionally be subjected to higher pH values. These carriers are stable over a wide temperature range (optionally at least from about 1° C. to at least about 45° C.). As a natural food product, this GRAS (generally recognized as safe) protein is biocompatible and biodegradable.

According to some embodiments, the present invention features a composition comprising micelles formed from an isolated beta casein under acid conditions below the pI of beta casein and preferably at least one pH unit, more preferably at least two pH units, below the pI of the beta casein. The micelles of the composition preferably comprise a majority of beta casein, optionally at least about 70%, preferably at least about 80%, more preferably at least about 90% and most preferably at least about 95% beta casein.

Embodiments of the invention enable incorporation of considerable amounts of additives, for example, bioactive compounds, into foods and beverages, keeping them stable for a long time in various pH environments. Without wishing to be bound by any theory or mechanism of action, the release of the additives from these beta-casein nano-encapsulators occurs due to protease activity in the gastrointestinal tract. The natural excellent digestibility of casein assures good release and superior bioavailability of the additives.

As noted above, it has now been found that these nanoparticulate β-casein carriers are unexpectedly stable at a wide low-pH range, and at a wide range of temperatures. As a natural, digestible food component, beta casein is biocompatible, and thus should not elicit immune responses against it. The beta-casein assemblies provide protection to fully or partially encapsulated additives in the harsh acidic environment of the stomach. The term "additives" may include any molecule or compound or combination of molecules or compounds that may be advantageously encapsulated in the nano-assemblies according to embodiments of the invention. Additives may include, among others, bioactive components having nutritional, therapeutic or cosmetic activity such as nutraceuticals and non prescription therapeutics. Additives may also include colorants, flavors and fragrances.

According to one embodiment the additive includes hydrophobic nutraceuticals, such as vitamin D or derivatives thereof.

According to one aspect, the present invention provides a composition for the enrichment of food and/or beverage, the composition comprising additive loaded beta-casein micelles wherein a majority of the micelles are of a diameter of about 100 nm or less. According to some embodiments the particle size of the loaded nano-assemblies is typically between 10 and 500 nm, more specifically between 20 and 200, more specifically between 25 and 100 nm. The size and distribution of sizes can be controlled by parameters of the composition, such as, the presence of salt, pH and temperature.

According to some embodiments the composition is at pH above the beta-casein pI (about 5.3). According to one embodiment the composition is at pH of about 7. According to this and other embodiments the composition may include a phosphate buffer.

According to some embodiments the composition is at pH is below the beta-casein pI. According to one embodiment the composition is at pH of between about 2 and about 4.2. According to this and other embodiments the composition may include lactic acid. According to some preferred embodiments the composition excludes added phosphate salts. According to some preferred embodiments the composition excludes added calcium atoms. Without wishing to be bound by any theory or mechanism of action, beta-casein micellar compositions of the present invention do not require calcium-phosphate bridges for their formation, both above and below the pI of the beta-casein.

The empty carrier and the loaded system are also stable in a wide ionic strength range from at least about 0.002 M to about 0.5 M. More typically, from at least about 0.002 M to about 0.2 M. Even more typically, from at least about 0.002 M to about 0.1 M.

According to some embodiments of the present invention the amount of the beta-casein in the composition is between about 0.05 and about 50%. More typically, the amount of beta-casein present in the composition is between about 0.5 and about 25%. Even more typically, the amount of beta-casein present in the composition is between about 0.5% and about 10%. Still more typically, the amount of beta-casein present in the composition is between about 0.5% and about 5%. Yet still more typically, the amount of beta-casein present in the composition is between about 0.5 and about 2%.

According to a second aspect, the present invention provides a method for the preparation of a solution for the enrichment of food or beverage, the method including the following steps:
  adding beta-casein to an aqueous solution selected from a buffer or an acid solution;
  mixing the solution at 1-45° C., preferably 4° C., to obtain a solution of beta-casein nano-assemblies; and
  adding a bioactive component to the solution of beta-casein assemblies to achieve a desired protein bioactive component molar ratio.

The bioactive component is preferably added during vigorous mixing of the beta casein assemblies.

The assemblies of the present invention can be prepared by adding the drug solubilized in ethanol to the beta-casein assemblies or micelles at acidic or neutral pH followed by stirring. Typically the amount of ethanol present in the composition or formulation is between 0.05 and about 20%. More typically, between about 0.1 and about 10%. Even more typically, between 0.1 and about 8%. Yet even more typically, between 0.1 and 5%. Alternatively, the assemblies of the present invention can be prepared by dry mixing the drug and beta-casein, and then adding the dry mixture to a buffer whereas the buffer is an acidic buffer or a neutral buffer. This procedure avoids the addition of ethanol. The buffer can maintain a pH either above or below the beta-casein pI. According to some embodiments the buffer pH is in the range of about 2 to about 4.2 (below the beta-casein pI). According to other embodiments the buffer pH is in the range of about 5.5-about 8.0 (above the beta-casein pI). More specifically the buffer pH is about 7.0.

According to one embodiment a lactic acid buffer or a phosphate buffer may be used.

According to one embodiment the solution may be mixed at temperatures ranging from about 1° C. to about 45° C., more preferably from about 4° C. to about 25° C., yet more preferably about 4° C. for at least one hour.

According to one embodiment the additive is a hydrophobic nutraceutical. According to one embodiment the additive is vitamin-D or a derivative thereof.

According to some embodiments the step of vigorously mixing the additive and solution of beta-casein assemblies includes periodically vortexing the additive and solution of beta-casein assemblies.

According to some embodiments the desired protein:additive molar ratio is between 1:1 to 1:20. According to some embodiments the desired protein:additive molar ratio is between 1:1 to 1:8. According to some embodiments the desired protein:additive molar ratio is between 1:2 to 1:16. According to another specific embodiment the desired protein:additive molar ratio is 1:1.

To produce a functional food or beverage the additive and beta-casein self-assemblies solution is added to a food or beverage. The functional food or beverage may be a neutral or acid milk product. According to one embodiment the functional food or beverage is a non fat food or beverage. According to some embodiments the functional food or beverage may include a low pH soft drink. According to one embodiment the functional food or beverage is a clear food or beverage, for example mineral water.

Embodiments of the invention provide novel beta-casein assemblies which are at a pH below the pI of beta casein.

According to one embodiment a method for forming beta-casein assemblies below the isoelectric point of beta casein includes the steps of adding beta-casein to a lactic acid solution and mixing the solution. According to one embodiment the lactic acid solution is an about 6 wt % solution. The lactic acid solution may be adjusted to a desired pH, according to one embodiment the lactic acid solution is adjusted to a pH in the range of about 2.0-about 4.2.

According to one embodiment the step of mixing is done at 4° C. According to one embodiment the step of mixing is done for at least 36 hours.

According to one embodiment the step of adding beta casein comprises adding protein to a concentration of above 0.1 mg/ml.

Embodiments of the invention provide the use of beta-casein micelles in the preparation of a functional clear food or beverage and the use of beta-casein micelles in the preparation of a functional acidic food or beverage.

Embodiments of the invention provide, for the first time, low-pH and higher pH stable micelles of beta-casein loaded with additives.

Beta-casein constitutes about 38% of the casein in bovine milk. Its primary structure is composed of 209 amino acids, and its molecular mass is 23,946 to 24,097 Da (depending on the genetic variant). It is the most hydrophobic casein because of its large hydrophobic C-terminal domain (based on its primary structure). However, its highly charged N-terminal domain, containing the phosphate center, makes it very amphipathic. The pronounced amphiphilic structure of β-Casein imparts many properties resembling those of low molecular weight surfactants. Thus, the protein tends to self-assemble under to appropriate conditions into well defined micelles of about 15 to about 60 molecules with a critical micelle concentration (CMC) in the range of 0.05-0.2%, depending on temperature, pH, solvent composition and ionic strength (Portnaya I. et al. 2006, J. Agric. Food Chem. 54; 5555-61).

The critical micelle concentration (CMC) is defined as the concentration of surfactant (in this case, the beta casein protein) above which micelles are spontaneously formed. Upon introduction of the protein into the system (such as for example the compositions described herein), the protein will initially partition into the interface, reducing the system free energy by a) lowering the energy of the interface (calculated as area×surface tension) and b) by removing the hydrophobic parts of the surfactant from contacts with water. Subsequently, when the surface coverage by the surfactants increases and the surface free energy (surface tension) has decreased, the surfactants start aggregating into micelles, thus again decreasing the system free energy by decreasing the contact area of hydrophobic parts of the surfactant with water. Upon reaching CMC, any further addition of surfactants typically increases the number of micelles.

These characteristics give micelles composed of at least a majority of beta-Casein proteins an advantage over the prior art casein micelles which size distribution cannot be controlled very well (typical sizes are 50-500 nm in diameter), such that their heterogeneity is large, and encapsulation is likely restricted.

According to at least some embodiments, the micelles of the present invention have a diameter of optionally up to about 300 nm, preferably up to about 200 nm or more preferably up to about 100 nm.

According to some embodiment of the present invention, the composition comprises micelles, wherein the micelles comprise isolated beta casein prepared at neutral pH, wherein the total content of beta casein of the micelles is at least about 70% wt/wt of the micelles, wherein the micelles have a diameter of optionally up to about 300 nm, preferably up to about 200 nm or more preferably up to about 100 nm.

U.S. Pat. No. 5,405,756 teaches that beta-casein tends to precipitate at pH values around the pI of the protein. The present invention, in at least some embodiments, overcomes this drawback of beta-casein by preferably preparing the micelles at a pH value that is at least about one unit, and more preferably at least about two units, the pI of beta-casein. Such a process may optionally comprise adding an acidifying agent, which may for example and without limitation optionally comprise any biologically or pharmaceutically compatible acid. According to some optional embodiments of the present invention, the process for preparation of the micelles involves a rapid rather than gradual reduction in pH as one non-limiting method for avoiding precipitation. Embodiments of the invention provide novel processes of forming beta-casein assemblies below the isoelectric point of beta casein and novel processes of loading beta-casein vehicles, below and above the isoelectric point, with, for example, water-insoluble food additives for enrichment of clear and/or nonfat, or other drinks or foods.

BRIEF DESCRIPTION OF THE DRAWINGS

Some embodiments of the invention are herein described, by way of example, and for purposes of illustrative discussion, with reference to the accompanying drawings, in which:

FIG. 4: (a) SAXS curves of β-casein solutions, obtained for different protein concentrations at pH 2.6 at 4° C. For better visibility, only each fifth experimental point of the scattering curves is shown. The forward scattering intensity was determined by fitting the experimental curves with the IFT routine including desmearing. (b) Aggregation numbers as a function of the concentration, determined from the scattering curves given in a.

FIG. 18: Vitamin D stability at pH 2.5, with and without beta-casein. (A) at t=0; (B) at t=7 days. In both (A) and (B) the right vial contains vitamin D only and the left vial contains a 1:2 beta-casein:vitamin D solution (beta-casein concentration: 0.5% wt).

FIG. 19: Vitamin D stability in aqueous solution, with and without beta-casein, at pH 2.5 and 7 at room temperature.

DETAILED DESCRIPTION OF THE INVENTION

Figure 1A:
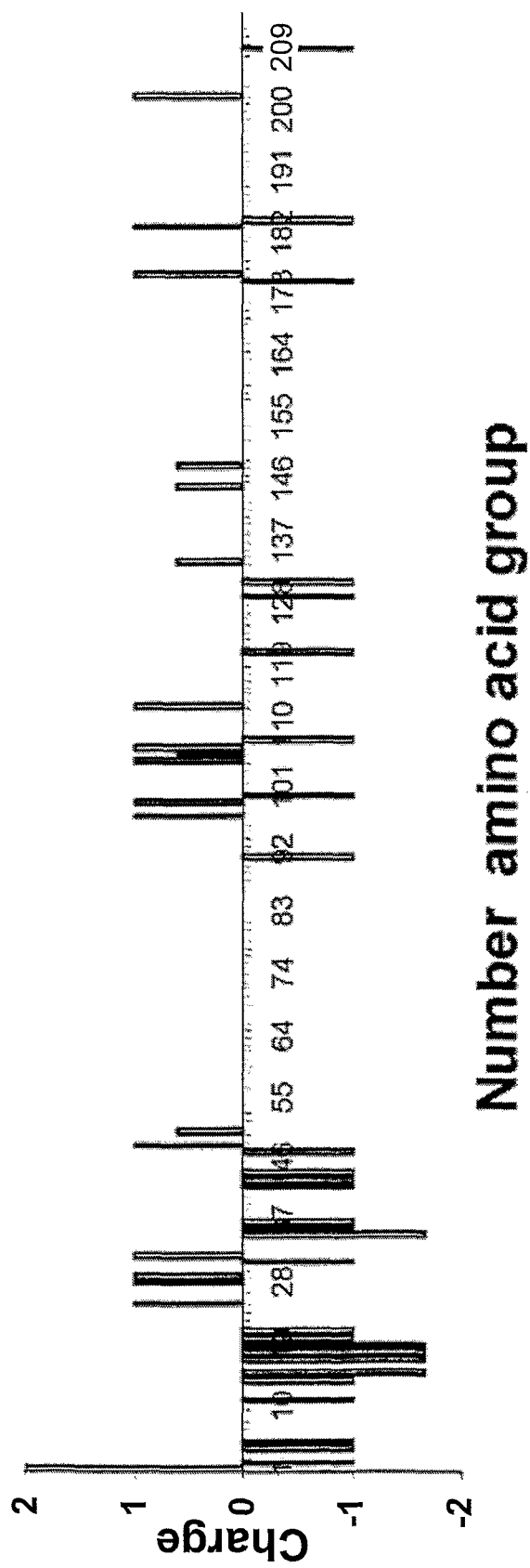
FIG. 1: Distribution of charges along the b-casein backbone at pH 6.7 (panel a) and pH 2.6 (panel b).

The present invention include the formation of nano-assemblies of the protein beta-casein (MW of ~24.0 kDa) and loading thereof with additives, at a pH at least one preferably at least two pH units above or below the pI of beta-casein (pI=5.3). According to some embodiments nano-assemblies can be loaded and kept stable at any pH within the range of 2.0-4.2. According to another embodiment nano-assemblies can be loaded and kept stable at a neutral pH, typically between 6.0 and 8.0, more specifically between 6.5 and 7.5 or at any pH within these ranges.

The present invention now discloses that the adsorption of hydrophobic additives, for example nutraceuticals, onto the hydrophobic domains of beta-caseins, and the formation of the micellar self-assemblies stabilize the hydrophobic compound in aqueous surrounding and protect them from degradation. Such beta-casein micelles-hydrophobic compound system facilitates the enrichment of low fat and fat free dairy and other food products, in particular liquid products, with the bioactive molecules, while minimizing the effect of the compound incorporation on the food properties in general and during processing. Encapsulation of biologically active compounds within beta-casein micelles is advantageous over hitherto known encapsulation methods as the micelles are a natural component of milk products and their nanometric size minimizes their effect on the food product sensory properties, including dairy as well as non dairy foods. In addition, when the active compound possesses undesirable attributes, the encapsulation in the micelles diminishes such unwanted features (e.g. in the case of omega 3 fatty acids). Another important potential benefit is the improved bioavailability of the enclosed compound due to its distribution, at a molecular level, over a very large surface area of the caseins in the nanoscopic micelles, and the fact that caseins are evolutionally optimized for ease of digestion and absorption. The open tertiary molecular structure of casein also facilitates effective proteolysis, leading to the release of the entrapped bioactives.

According to one embodiment hydrophobic nutraceuticals are loaded into the nano-assemblies. According to one embodiment vitamin D and/or a derivative of vitamin D is loaded into the nano assemblies.

According to another embodiment the hydrophobic nutraceuticals loaded into the nano assemblies are selected from the following unlimited list including: any one of a class of dietary supplements, vitamins, minerals, plant extracts, phytochemicals, healing or disease-preventative foods that have medical or pharmaceutical effects on the body. Examples for non-polar or hydrophobic nutraceuticals include, but are not limited to fatty acids (e.g., omega-3 fatty acids, ALA, DHA and EPA); fruit and vegetable extracts; vitamins A, D, E and K; phospholipids, e.g. phosphatidyl-serine; certain amino acids (e.g., iso-leucine, leucine, methionine, phenylanine, tryptophan, and valine); various food additives, various phytonutrients, for example lycopene, lutein and zeaxanthin; isoflavones and polyphenolic substances, certain antioxidants; plant oils; and fish and marine animal oils and algae oils.

According to other embodiments the additives selected from bioactive compounds having nutritional, therapeutic or cosmetic activity such as nutraceticals or non prescription therapeutics are loaded into the nano-assemblies. Combinations of additives may also be loaded into-nano-assemblies. According to further embodiments colorants, flavors, fragrances or a combination thereof may be loaded into nano-assemblies.

According to some embodiments assemblies can be produced and kept stable at different pH values by using appropriate buffers (e.g. phosphate or lactate).

According to one embodiment encapsulation below the pI of beta-casein is done by dissolving the beta-casein in a low-pH solution (e.g. a lactic acid solution). According to another embodiment, encapsulation above the pI of beta-casein is done by dissolving the beta-casein in water, or an aqueous buffer solution (e.g., phosphate buffer solution) at the desired pH.

According to embodiments of the invention beta-casein nano-assembly size increases upon incorporation of sensitive nutraceuticals in a stable form, but loaded assemblies can be kept under 150 nm in size to maintain clarity of their solutions. According to some embodiments nano-assemblies can be kept under 100 nm in size. According to some embodiments nano-assemblies can be kept under 80 nm in size. In non clear products the size of the loaded beta-casein vehicles will be dictated mainly by colloidal stability, and smoothness criteria, and can thus reach several hundreds nanometers.

The beta-casein micelles according to embodiments of the invention are made of all GRAS components and may be loaded with hydrophobic or other nutraceuticals and additives, for enrichment of nonfat, low fat and other foods and beverages including clear ones, without compromising transparency, or other sensorial property of the food or beverage, and while providing stability and protection to the encapsulated additives. Solutions according to embodiments of the invention can be added to low-pH soft drinks, to neutral or to acid milk products, like yoghurt, to fermented milk products containing acidic fruit juices concentrates, to fruit juices, and even to mineral water.

According to some embodiments assemblies typically contain protein concentrations of above 0.1 mg/ml. According to some embodiments the nano-assemblies are produced at a temperature of between 1° C. and 60° C.

Concentrated colloidal systems according to embodiments of the invention are typically isotropic and may be slightly opalescent, however at the desired target dosage concentration of the added nutraceutical (e.g. vitamin D), the systems are transparent both above and below the pI of the beta-casein. A solution of nano-assemblies stored at 4° C. is stable for several weeks.

Some aspects of embodiments of the invention will be described in the following examples. The materials, methods, and examples discussed below are illustrative and are not intended to limit the scope of the invention.

EXAMPLES

Methods

Cryo-TEM: Specimens were prepared in the controlled environment vitrification system (CEVS) (Bellare et al. *Electron Microsc. Technique*, 1988, 10; 87-111) at 24° C. and 100% relative humidity to avoid loss of volatiles. First, the solutions were incubated in the CEVS at the desired temperature for 1 h. Then, a 7 µL drop of each solution was placed on a TEM copper grid covered with a perforated carbon film (Pelco International) and blotted with filter paper to form a thin liquid film of the sample (100-200 nm thick). The thinned sample was plunged into liquid ethane at its freezing temperature (−183° C.) to form a vitrified specimen and then transferred to liquid nitrogen (196° C.) for storage. The vitrified specimens were examined in a Philips CM120 transmission electron microscope operating at an accelerating voltage of 120 kV. We used an Oxford CT3500 (Oxford Instruments) cryoholder that maintained the specimens below −175° C. during sample transfer and observation. Images were recorded digitally on a cooled Gatan MultiScan 791 CCD camera using DigitalMicrograph 3.1 software (Gatan) in the low-dose imaging mode to minimize beam exposure and electron-beam radiation damage.

ITC: ITC measurements were performed with a VP-ITC calorimeter (MicroCal) at a temperature of 24° C. The reaction cell (V=1.43 mL) was filled with degassed solvent (lactic acid at pH 2.6, or phosphate buffer at pH 7.0). The injector-stirrer syringe (289 µL) was loaded with a beta-casein micellar solution (20 mg/mL). The micellar solution was injected into the reaction cell in 28 steps of 10 µL aliquots each, and the heat flow was measured. During the titration, the stirring speed was 310 rpm. The duration of each injection was 20 s, and the equilibration time between consecutive injections was 3 min. Such an interval was sufficient to equilibrate the reaction cell after every injection. Each experiment was performed at least three times. Calorimetric data analysis was carried out using Origin 5.0 software (MicroCal).

Analytical Ultracentrifugation: Sedimentation equilibrium experiments were performed at 24° C. using a Beckman Optima XL-A (Palo Alto, Calif.) analytical centrifuge at 6000, 10000, and 12000 rpm for the low-pH solutions and at 4000, 6000, and 8000 rpm for the pH 7.0 solutions. Data were collected at 280 nm. The beta-casein solutions were studied at concentrations ranging from 0.2 to 10.0 mg/mL at pH 2.6 and from 0.2 to 2 mg/mL at pH 7.0 and an ionic strength of 0.1. Past studies showed that the protein self-assembly is not affected by pressure and, therefore, it is not speed-dependent. The average apparent molecular weight of the micelles at the various protein concentrations was calculated following methods well known in the art (The partial specific volume vj of the solute was taken to be 0.742 cm3/g3, and a solution density F of 1.0044 g/cm3 was measured). At beta-casein concentrations of 2 mg/mL and above under low pH conditions, the plot of the natural logarithm of the measured absorbance versus the square of the radius from the axis of rotation was not linear. To estimate Nagg, the limiting slope toward the outer edge of the sample cell was used to provide $d\ln(c)/dr^2$. The molecular weight calculated using this slope was divided by the monomer molecular weight calculated from the beta-casein amino acid sequence (24000).

Small Angle X-ray Scattering (SAXS): The small angle x-ray scattering equipment consisted of a SAXSess camera (Anton-Paar, Graz, Austria) connected to an x-ray generator (Philips, PW1730/10) operating at 40 kV and 50 mA with a sealed-tube Cu anode. A Göbel mirror was used to convert the divergent polychromatic x-ray beam into a focused line-shaped beam of Cu Kα radiation (λ=0.154 nm). The 2D scattering pattern was recorded by a PI-SCX fused fiber optic taper CCD camera from Princeton Instruments, which is a division of Roper Scientific, Inc. (Trenton, N.J., USA). The used CCD detector features a 2084×2084 array with 24×24 µm pixel size (chip size: 50×50 mm). The CCD was operated at −30° C. with 10° C. water-assisted cooling to reduce the thermally generated charge. Cosmic ray correction and background subtraction were performed on the 2D image before further data processing. The 2D image was integrated into the one-dimensional scattering function within a band of 10 mm. The measurement time was 30 min for each scattering curve (6 images of 5 minutes were taken to assist the cosmic ray correction).

Determination of the Beta-Casein Assemblies Molecular Weights.

The molecular weight of the scattering aggregates were calculated according to Eq. 1:

$$M = \frac{d\Sigma(0)}{d\Omega}(N_A/c\Delta\rho_M^2) \quad (1)$$

where M is the molecular weight, $d\Sigma(0)/d\Omega$ (cm$^{-1}$) the forward scattering intensity at q=0, c (g/cm$^3$) the beta-casein concentration, $N_A$ the Avogadro number, and $\Delta\rho_M$ (cm/g) the scattering length difference per mass, given by:

$$\Delta\rho_M = \Delta\rho\bar{v} \quad (2)$$

The scattering length difference $\Delta\rho$ (cm$^{-2}$) was calculated using the known chemical composition of the protein and the solvent, and $\bar{v}$ (cm$^3$/g), the specific volume of the protein in the solution that was calculated via density measurement of the solvent and the solution. The micelle aggregation number was then calculated by dividing the molecular weight of the micelles determined with Eq. 1, by the molecular weight of a single protein molecule.

PDDF Determination.

For a particle of arbitrary shape with a scattering density difference of $\Delta\rho(r)$, the pair distance distribution function p(r) (PDDF) is given by:

$$p(r) = r^2 \overline{\Delta\rho^2}(r) \quad (3)$$

where $\overline{\Delta\rho^2}(r)$ is the convolution square of $\Delta\rho(r)$ averaged for all directions in space. The PDDF is related to the scattered intensity I(q) by a Fourier transformation, and it enables the determination of the overall shape and size of the scattering objects.

$$I(q) = 4\pi \int_0^\infty p(r) \frac{\sin(qr)}{qr} dr \quad (4)$$

where q is the magnitude of the scattering vector q, defined as $$q = \frac{4\pi}{\lambda}\sin\left(\frac{\theta}{2}\right) \quad (5)$$

λ is the wavelength of the incident radiation and θ is the angle between the scattered and incident beam. The function $$f(r) = p(r)/r \quad (6)$$

is useful to identify flat plate-like particles, although it has no direct physical meaning. For lamellae, this function starts with a linearly increasing part and becomes almost flat when r is equal to the thickness of the lamella. For flat particles with a finite base area, the outer part decreases linearly because of boundary losses. The thickness of the lamella can then be read from the transition point. Hence, in practice, the shape of the function $f(r)$ allows the recognition of lamellar particles and determination of their thickness.

Statistical Analysis: For each of the methods applied, a statistical analysis of the data was performed, based on at least three separate replicate experiments. The standard error of the ITC data was found to be no more than 5% for the CMC and micellization relative cooperativity (MR) values and no more than 3% for $\Delta H$demic. The standard error of the analytical ultracentrifugation data is 5%, and that of the Rg is 4%. The analysis supports the statistical significance and validity of the results.

Example 1

Preparation of beta-casein assemblies: weighted amounts of lyophilized bovine beta-casein are dissolved in low-pH solution (e.g. ~6% by weight of lactic acid solution or hydrochloride acid solution, ~pH 2.1), typically at concentrations ranging from 0.1 mg/mL up to at least 50 mg/ml, to the desired pH (2.5-2.8), below the pI. The pH can be adjusted to the desired values using appropriate buffers. Mixing is done at room temperature, and the solution is equilibrated at 4° C. for ~36 hr, allowing complete solubilization and formation of the protein assemblies. Thereafter, the solutions can be held at any temperature between 1 and 60° C. Similarly, to prepare beta-casein micelles at neutral pH, weighted amounts of lyophilized protein are added to a buffer at neutral pH (e.g., HEPES buffer, or PBS), at concentration ranging from 0.1 mg/ml to ~40 mg/ml. Complete solubilization of the protein is achieved within ~36 hr, at 4° C. A transparent solution is obtained, containing unique nano-sized beta-casein assemblies. The protein solutions are filtered through a porous membrane of 0.45 micron pore size. The beta-casein concentration was determined by measuring the absorbance at 280 nm by an Ultrospec 2000 UV/Visible spectrophotometer (Pharmacia Biotech, England), using an extinction coefficient of $4.6_{(1\%)}$ mM$^{-1}$cm$^{-1}$. The stock solution is diluted with an acidic solution having the same pH, to the final concentration required, typically between 0.1 mg/ml and 20 mg/ml. The ionic strength and Osmolarity can be adjusted by mixing the micelles-containing solution with a salt or buffer solution, both having the same pH. The solution can be stored at 4° C., for at least several months (if sterile), depending on the storage medium pH and ionic strength.

The novel low and neutral pH beta-casein assemblies of the present invention have been characterized by various techniques including: isothermal titration calorimetry (ITC), small-angle x-ray scattering (SAXS), analytical ultracentrifugation, density measurements and cryogenic-transmission electron microscopy (cryo-TEM).

Example 2 beta-casein charge distribution: The distribution of charges along the beta-casein backbone and the beta-casein protein total charge at acidic and neutral pHs were calculated. To estimate the net charge and the charge distribution of beta-casein at pH 2.6, we used a procedure similar to that reported by Ribadeau et al. 1972, *Eur. J. Biochem.*, 25:505-14. The degree of protonation, $\theta i$, A of the individual titratable sites was calculated from the Henderson-Hasselbach equation. This equation is not valid when strong electrostatic interactions exist between titratable sites but can be used when the protein is in an unfolded state. Because beta-casein has an open structure, the equation is appropriate for calculating its net charge at low pH.

Figure 1B:
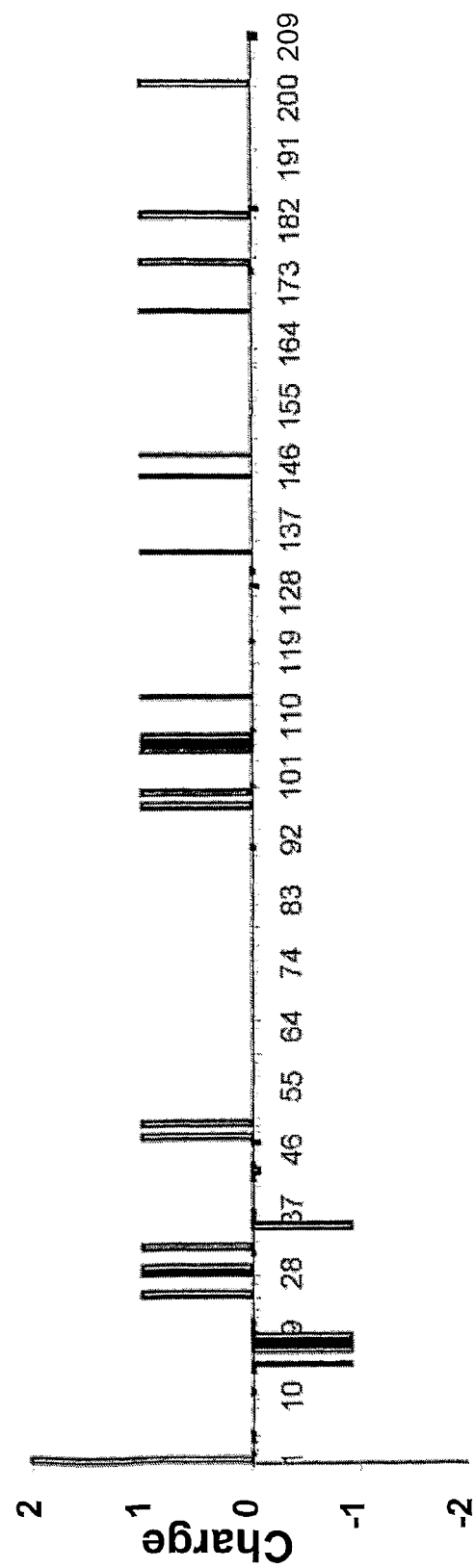
Figure 2A:
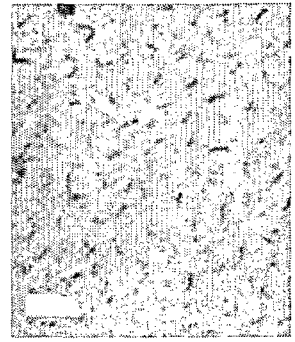
FIG. 2: Cryo-TEM images of 2 wt % β-casein micelles in lactic acid solution (pH 2.6): (panels a and b) 40° C., (panels c and d) 25° C., (panels e and f) 4° C. Panels a, c and e show low magnification regions populated with the protein micelles. Higher magnifications of these structures are given in panels b, d and f. All images show flat disc-like (plate-like) micelles. Due to the relatively low contrast of the thin micelles they are best seen when their flat surfaces are positioned parallel to the electron beam. In very thin specimens (e.g., image d) less structures and solvent (per unit volume) contribute to the 2-dimensional image, thus the micelles look more spaced, and additionally, micelles oriented with their flat surface perpendicular to the electron beam are also resolved (see, for example, the upper part of panel c, and the micelles enclosed in the dashed square in panel d). Arrows in the images point to few disc micelles, showing they have similar thickness and length under all the temperatures studied. Bar equals 50 nm (a, c and e) and 20 nm (b, d and f).
Figure 2B:
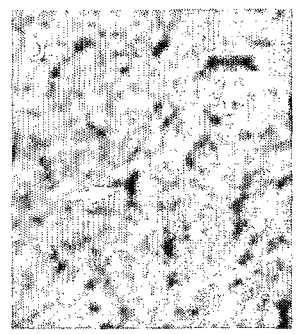
Figure 2C:
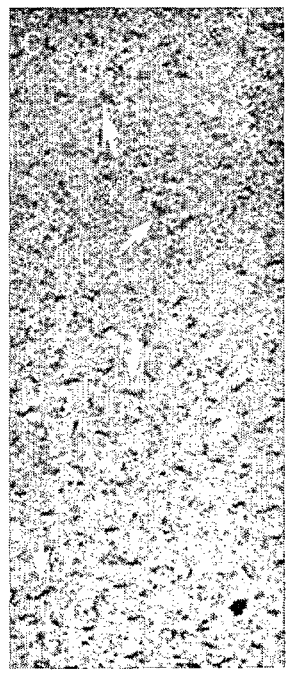
Figure 2D:
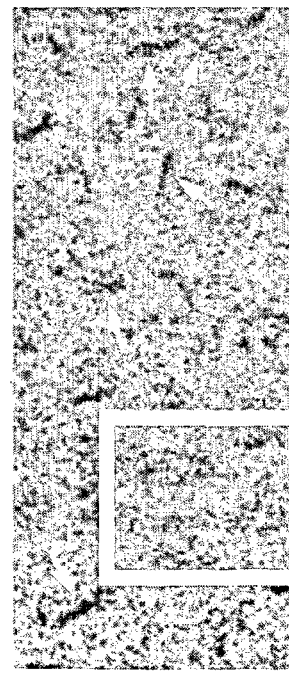

FIG. 1 shows the distribution of charges along the protein sequence at the two pH regimes. At pH 6.7, most charges are concentrated at the N-terminus, while the long C-terminus is highly hydrophobic. A net charge of −13.28 was calculated at this pH, in good agreement with previous calculations at similar pH values. At a low pH of 2.6, the absolute value of the protein net charge is somewhat larger [+15.82] vs [−13.28]). The charge distribution, however, changes significantly. A cluster of negative charges is present in sequences 15-20. Sequences 25-50 contain a cluster of six positive charges and in 97-113 another cluster of six charges exists, while the domain in between does not have any charge. Additionally, a large number of positive charges are distributed along the hydrophobic C-terminus domain. Thus, overall, this picture indicates that in an acidic environment, the protein loses the distinct separation between hydrophilic and hydrophobic domains.

Example 3

Characterization of the beta-casein micelles by cryo-TEM: The structural characteristics of the micelles in the two pH environments were studied by cryo-TEM and SAXS. Cryo-TEM was used to determine the shape of the micelles and to estimate their dimensions between 4 and 40° C. This information was further used to accurately calculate by SAXS the micelles' dimensions and to study how the size and shape are affected by temperature. SAXS measurements also provided the critical micelle concentration (CMC) and the micelle aggregation numbers as a function of temperature. Experiments were performed in the concentration range of 0.1-40 mg/mL protein, at low pH (between 2.1 and 2.6) in dilute lactic acid solution (6 wt %) or HCl and in aqueous solutions at pH 6.7 in the presence of 0.05M NaCl.

In the lactic acid solution (pH 2.6), flat disk-like micelles formed within the complete temperature range studied (4-40° C.), as shown in the cryo-TEM images presented in FIG. 2. From the 2-D projection of the micelles in the vitrified samples, we estimate that the micelles are 3-4 nm thick and that they have elongated surfaces 20-25 nm in length. Micelles of similar shape and dimensions also form in HCl at the same pH at room temperature. This suggests that under the conditions studied, the nature of the solvent's counterion has little, if any, effect on the 'beta-casein aggregates' size, shape, and dimensions. Overall, the cryo-TEM experiments show that at low pH, beta-casein self-organizes into a homogeneous population of flat, disk-like micelles, whose shape and dimensions appear to be independent of the solvent counterion or the solution temperature.

We further determined the self-assembly behavior of the solution of 20 mg/mL beta-casein at pH 6.7 and 0.05M NaCl as a function of temperature. Flat micelles were observed at 4° C. and 10° C., but their contrast is relatively low, and consequently, their morphology is somewhat indistinct. At 16, 25, and 40° C., oblate micelles were detected. Relatively spheroidal micelles were found at the high temperature of 60° C.

Example 4

Figure 3A:
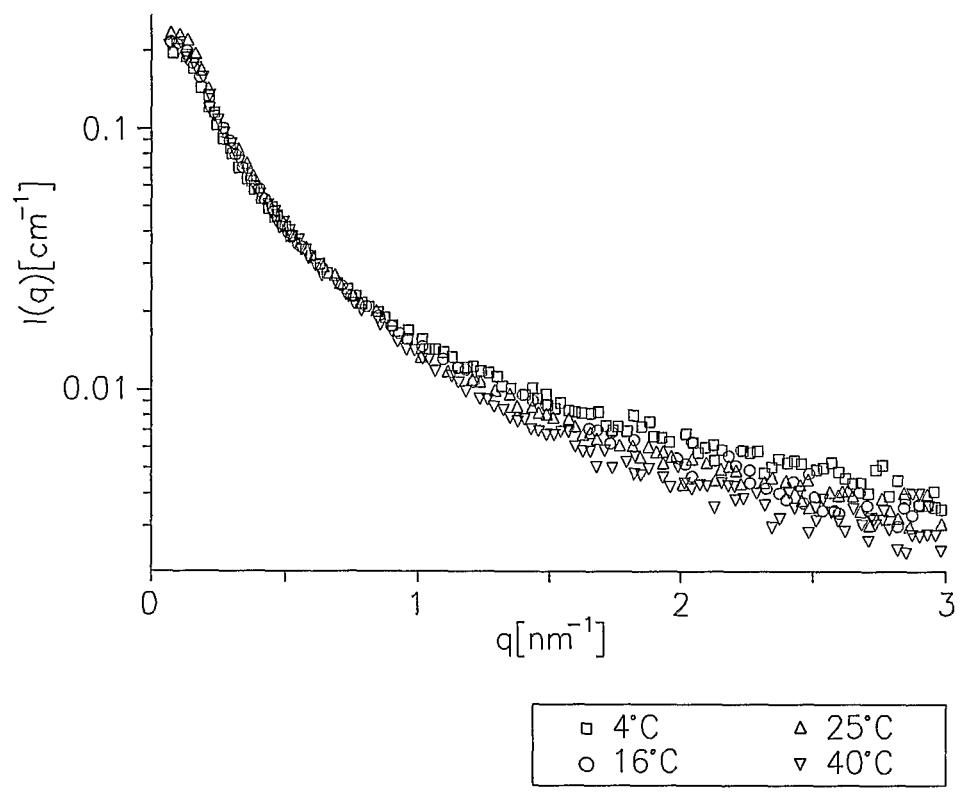
FIG. 3: (a) SAXS curves of 2 wt % β-casein solution at pH 2.6, at different temperatures. For better visibility, only each fifth experimental point of the scattering curves is shown. (b) Pair Distance Distribution Function (PDDF) obtained from the scattering curves by Indirect Fourier Transform (IFT). The area, which is proportional to the aggregation number, does not change significantly. The aggregation number was found to be similar at all temperatures. (c) Normalized PDDF deviates in shape from a homogenous sphere. rmax is the value of r where the PDDF has its maximum. (panel d) The function $f(r)$ indicates a plate-like particle shape with particle thickness of approximately 3.5 nm.
Figure 3B:
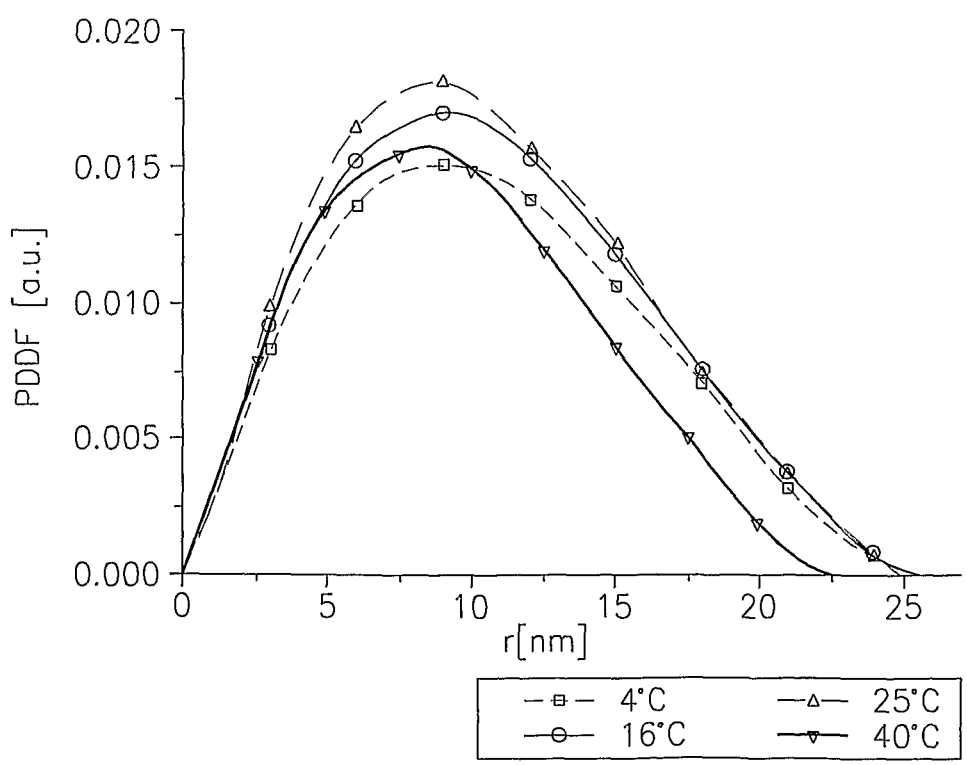
Figure 3C:
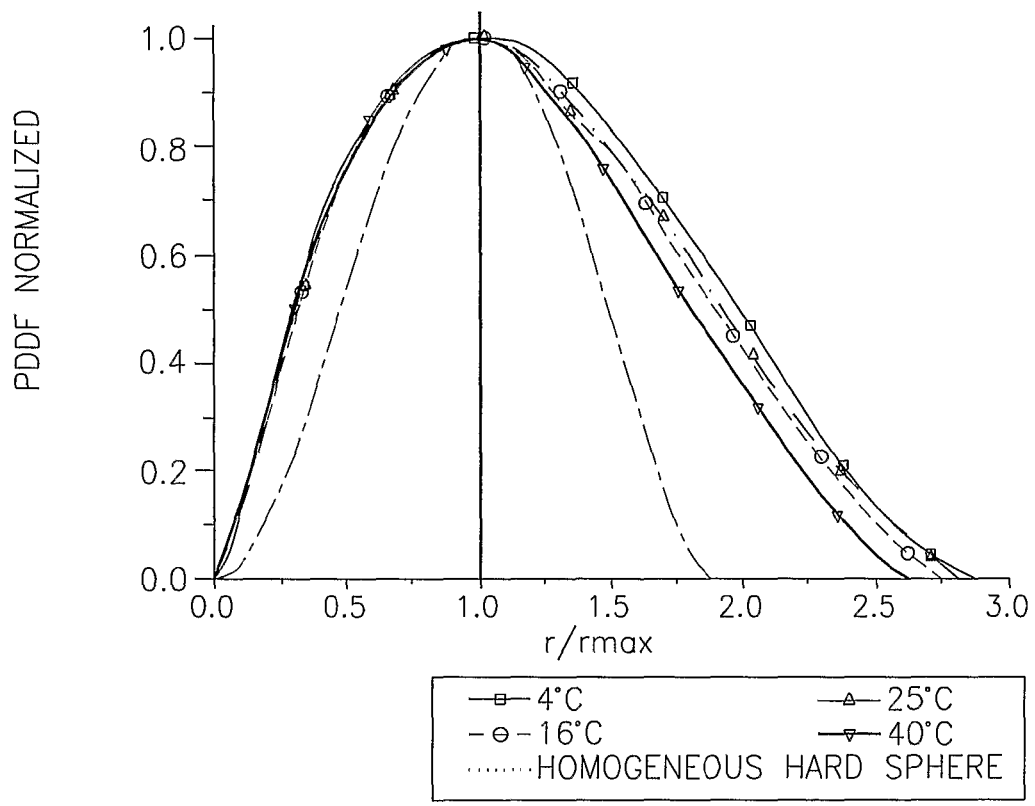
Figure 3D:
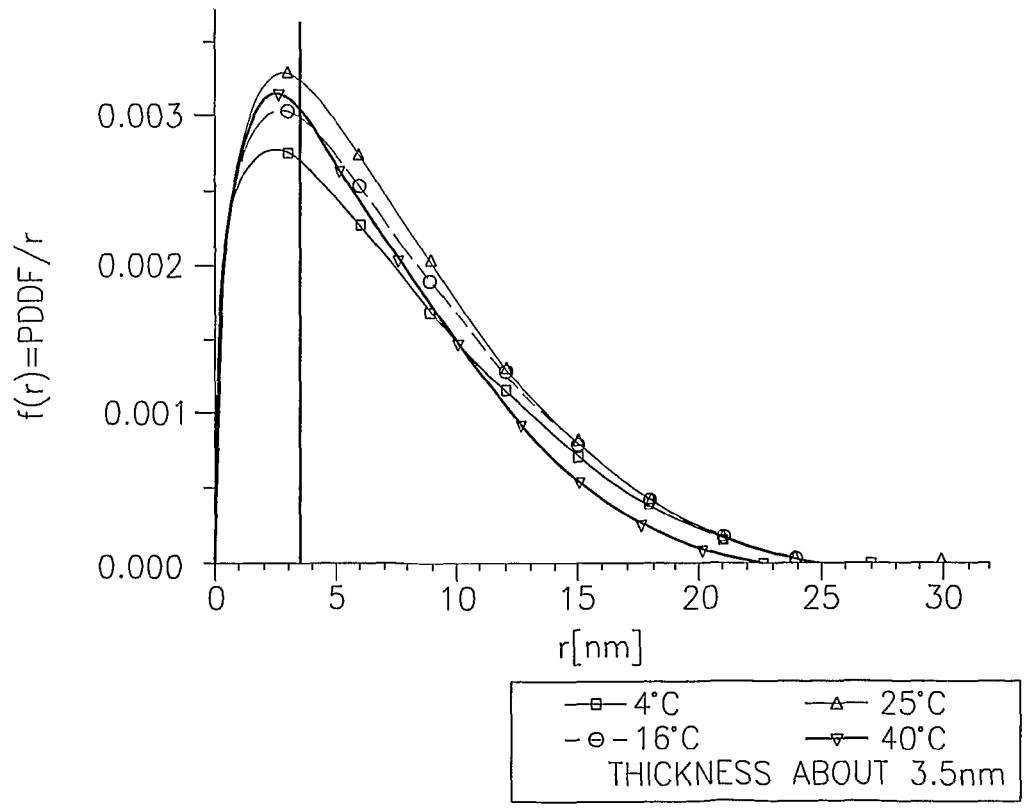

Characterization of the beta-casein micelles by SAXS: We have applied SAXS measurements to determine the shape and dimensions of the micelles at low pH and at neutral pH, more precisely, and to evaluate the micelle molecular weight (i.e., the aggregation number). The scattering curves of 20 mg/mL beta-casein in lactic acid solution (pH 2.6, IS 0.0022) at different temperatures are shown in FIG. 3a. Interestingly, very little change in the scattering curves is observed in the complete range of temperatures studied (between 4 and 40° C.), as we also found by cryo-TEM (FIG. 2). Consequently, the calculated Pair Distance Distribution Functions (PDDF), are also similar (FIG. 3b). The maximum micelle dimension is approximately 25 nm at all temperatures. The area under the PDDF curve, which is proportional to the weight of one particle, is almost constant. To calculate the aggregation number, the density of the solvent and the solution was measured at various temperatures (Table 2). The aggregation number was found to vary only slightly (between 8 and 11) as the temperature was raised from 4 to 40° C. (Table 2). These differences are not significant, and they indicate that the micelle aggregation number remains practically constant within this wide range of temperatures, as was also indicated by the constant scattering profiles shown in FIG. 3a,b.

The shape of the PDDF gives information on the shape of the assemblies. The experimental PDDFs were compared with a theoretical PDDF of a homogeneous sphere, and all functions were normalized to a value of 1 at the x- and y-axes at the PDDF maximum (FIG. 3 panel c). It can be clearly seen that the micelles have a very similar shape at different temperatures. However, the particles' shape deviates strongly from the shape of a sphere. In fact, the curve shape is characteristic of scattering from flat, plate-like particles, as indeed was indicated by the cryo-TEM data (FIG. 2). As expected for flat particles, the function $f(r)$ (FIG. 3 panel d) displays a peak after which it decreases almost linearly to the maximum dimension. From the transition point, which is marked with a line in FIG. 3d, the thickness of the particles was found to be close to 3.5 nm at all temperatures.

Figure 4A:
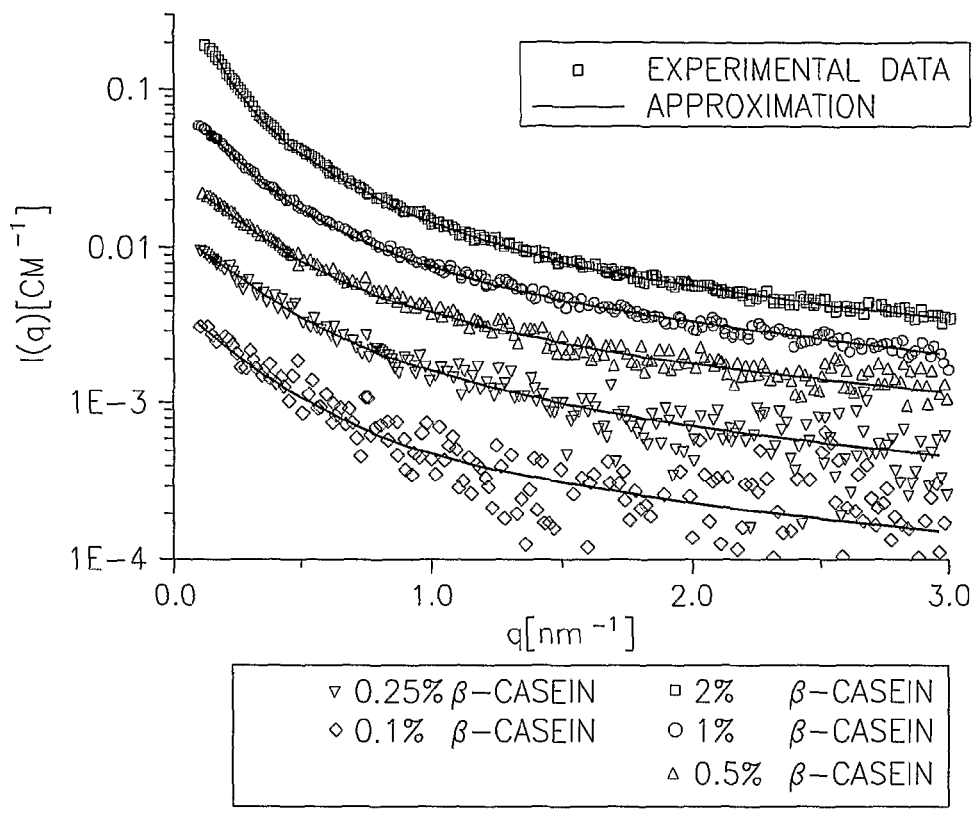
Figure 4B:
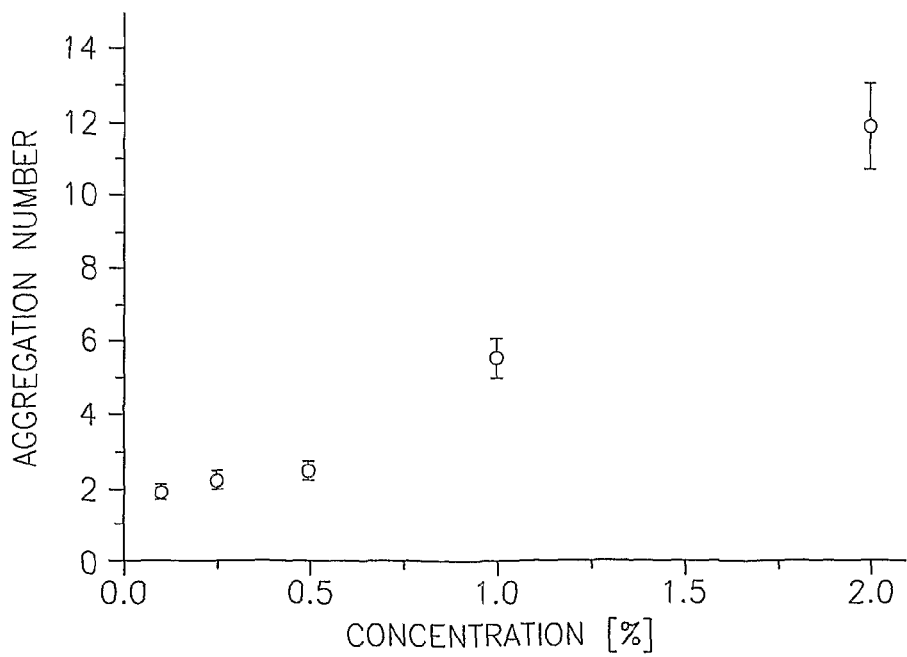

To determine the CMC and to investigate how the concentration affects the aggregation number, a series of dilutions, from 2.0 to 0.1 wt %, was prepared. The scattering curves were measured at 4° C. and were put on an absolute scale. The curves after subtraction of the solvent data are shown in FIG. 4a. As expected, the intensity of the scattering decreases when the concentration is decreased. But, in addition, there is also a change in the shape of the scattering curve. The upturn at low scattering angles is less pronounced at low concentrations, which indicates the presence of smaller particles. A detailed data evaluation described in the Experimental Procedures leads to the aggregation numbers shown in FIG. 4b. It is seen that above 0.5 wt %, Nagg strongly increases with the concentration, and at concentrations of 0.5 wt % and below, Nagg stays basically constant at a value of approximately 2. From this graph, the CMC of beta-casein is estimated to be around 0.5 wt % at 4° C. We have performed an equivalent experiment at 25° C. in which we reveals monomers at the limit of dilution (0.1 wt %), dimers at 0.25 wt %, and a notable increase into higher oligomers at higher concentrations, suggesting that the cmc at 25° C. is in the range of 0.1-0.25 wt %. The decrease in the cmc (from 0.5 to 0.1-0.25 wt %) upon raising the temperature from 4 to 25° C. is also reasonable and may be explained by larger hydrophobic interactions at 25° C. than at 4° C., which drive the aggregation to occur at lower concentrations.

Figure 5A:
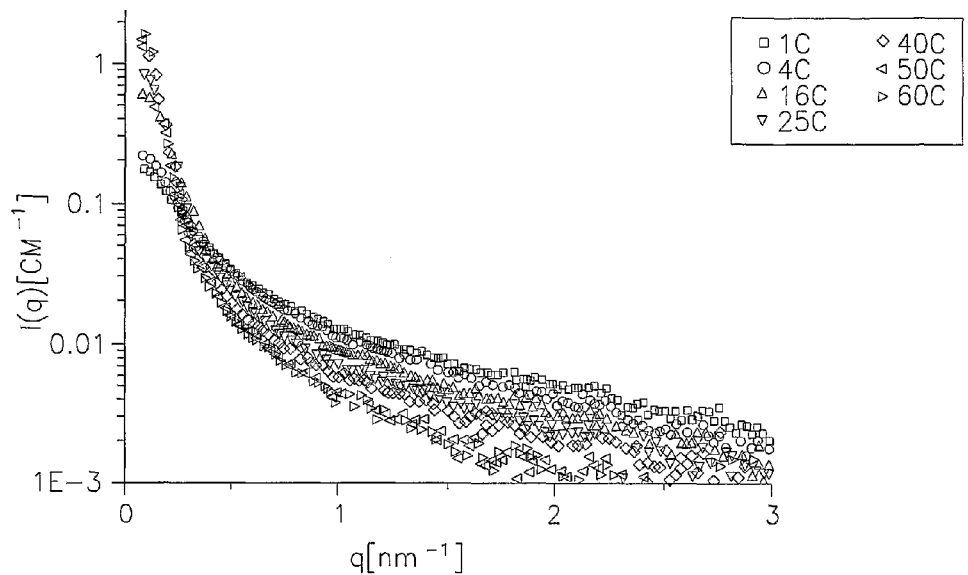
FIG. 5: (a) SAXS curves of a 2.0 wt % β-casein solution (pH 6.7) containing 0.05 M NaCl, at different temperatures. For better visibility, only each fifth experimental point of the scattering curves is shown. (b) The aggregation numbers determined from the scattering curves shown in panel a. The aggregation numbers increase with temperature. (c) PDDF obtained from the scattering curves by IFT. The area, which is proportional to the aggregation number, increases with temperature. (d) Normalized PDDF to show the deviation in shape from homogeneous monodispersed spheres.
Figure 5B:
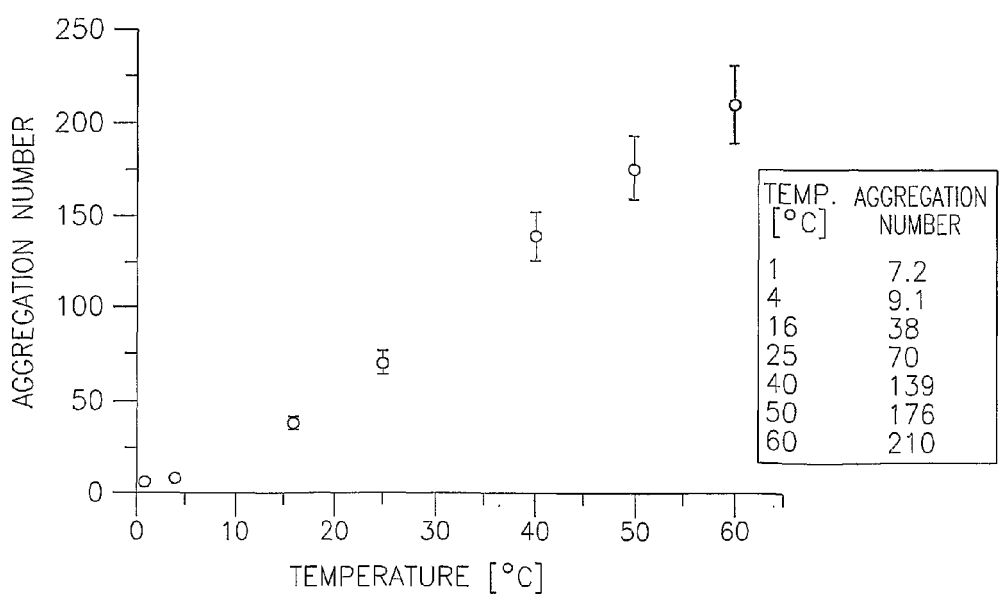
Figure 5C:
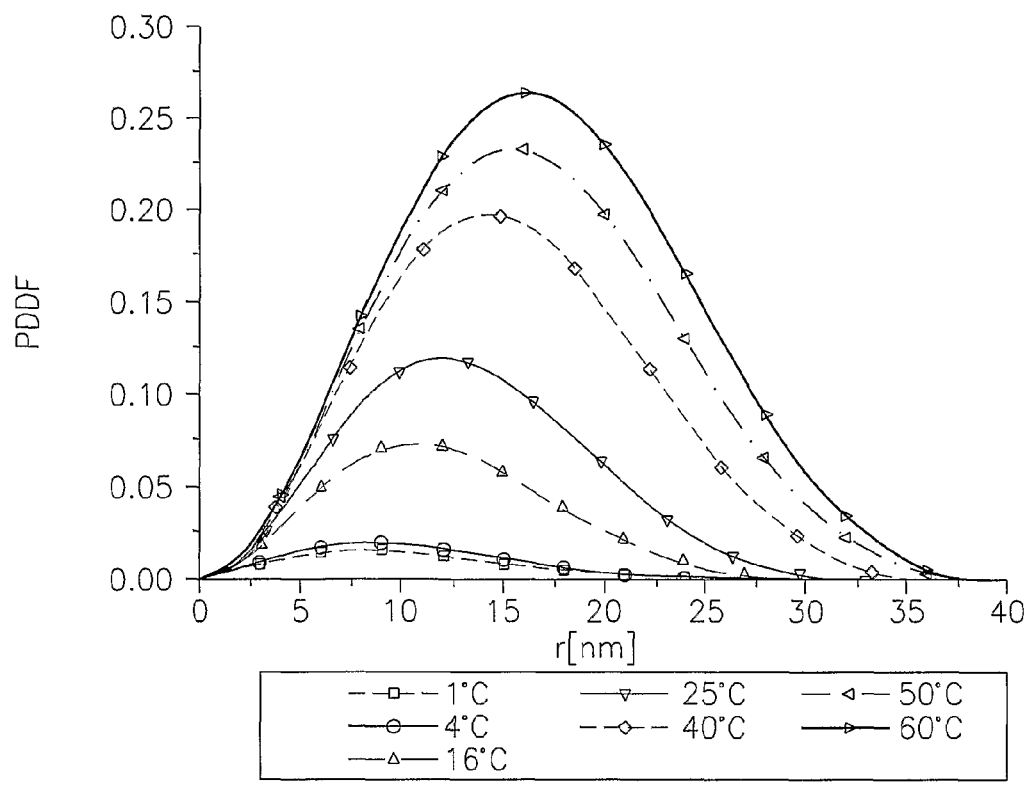
Figure 5D:
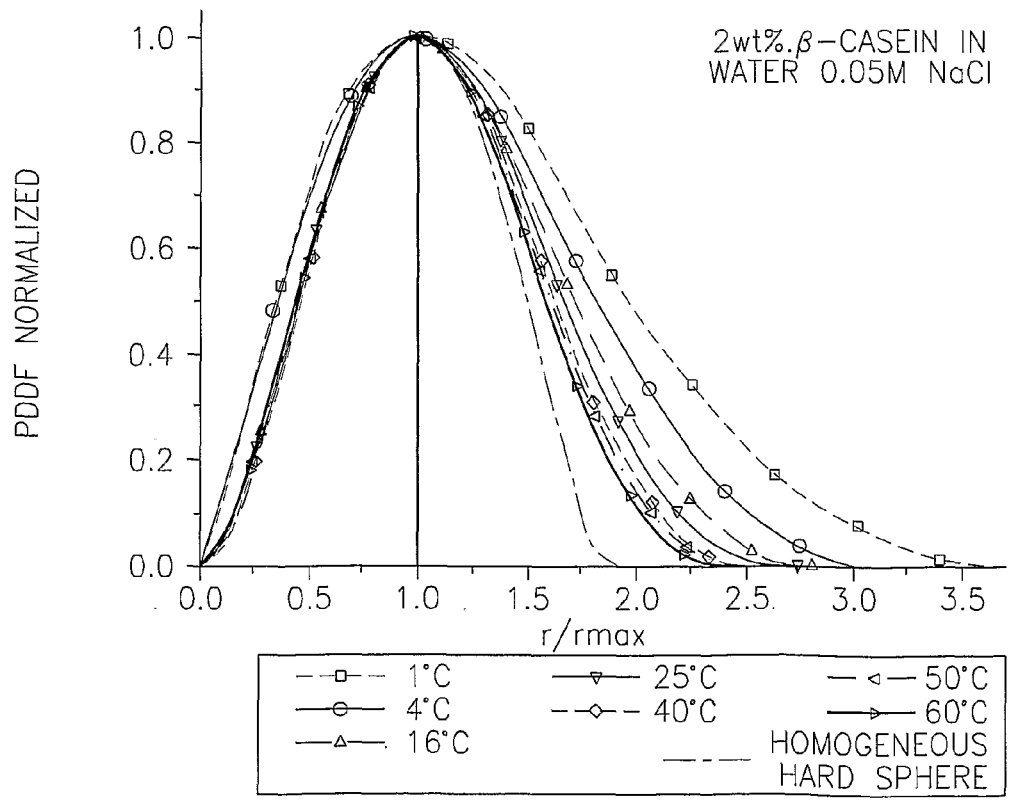

We further characterized the beta-casein micelles (20 mg/mL protein solutions) at pH 6.7 in the presence of 0.05M NaCl at various temperature between 1 and 60° C. (FIG. 5a). It is seen that the forward scattering intensity increases significantly in the low q regime but becomes smaller at high q values, as the temperature is increased. The aggregation numbers calculated from these data are shown in FIG. 5b. We find that the aggregation number increases from 7 to 210 as the temperature is raised from 1 to 60° C. As a result of the changes in the micelle dimensions, the area of the PDDF increases as well (FIG. 5c). The maximum dimension, which can be read from the point where PDDF reaches zero, grows from approximately from 25 to 40 nm. The shape of the micelles also changes upon heating. At low temperatures (4° C.), we found plate-like micelles, similar to those existing at low pH. Interestingly, the deviation from the PDDF of a sphere is similar to that found at pH 2.6. However, the scattering data indicate that as the temperature is increased to 16° C. and above, the assemblies become more spheroidal in shape, which fits well with the formation of oblate and, at higher temperatures, more spherical micelles. As the temperature is raised further, the normalized PDDF curves show an almost perfect overlap with the theoretical curve of the sphere (FIG. 5d). No further growth was observed above 50° C.

TABLE 2

Characteristic properties of the micellar solutions and the micelles determined by SAXS as a function of temperature at acidic pH environment.

| pH | T, (° C.) | CMC (wt %) | $N_{agg}$ | Micelle Shape | Micelle Dimensions |
|---|---|---|---|---|---|
| 2.6 | 4 | 0.5 | 8 | disc | Constant |
|  | 16 | ND | 10 | disc |  |
|  | 25 | 0.1-0.2 | 11 | disc |  |
|  |  | 0.19* | 6* |  |  |
|  | 40 | ND | 9 | disc |  |

ND—not determined;
*the CMC was found by isothermal titration calorimetry (ITC).
$N_{agg}$ was determined by sedimentation equilibrium.

Example 5

Figure 6A:
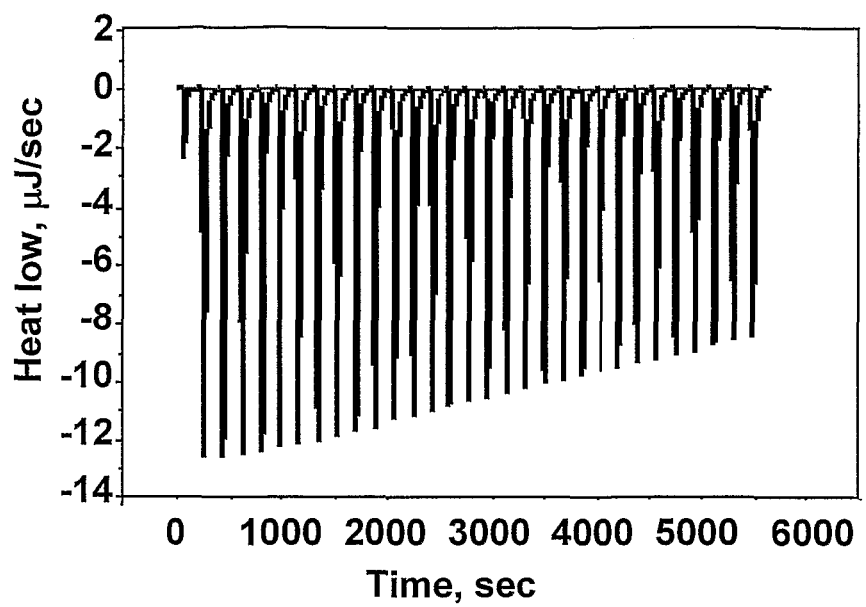
FIG. 6: Titration of micellar (20 mg/ml) β-casein solution in diluted lactic acid (pH 2.6) at very low ionic strength (0.002) into lactic acid solution, having the same pH and ionic strength, at 24° C.: (A) calorimetric traces, (B) reaction enthalpy vs. β-casein concentration in the cell, (C) first derivative of curve B calculated from the interpolated values.
Figure 6B:
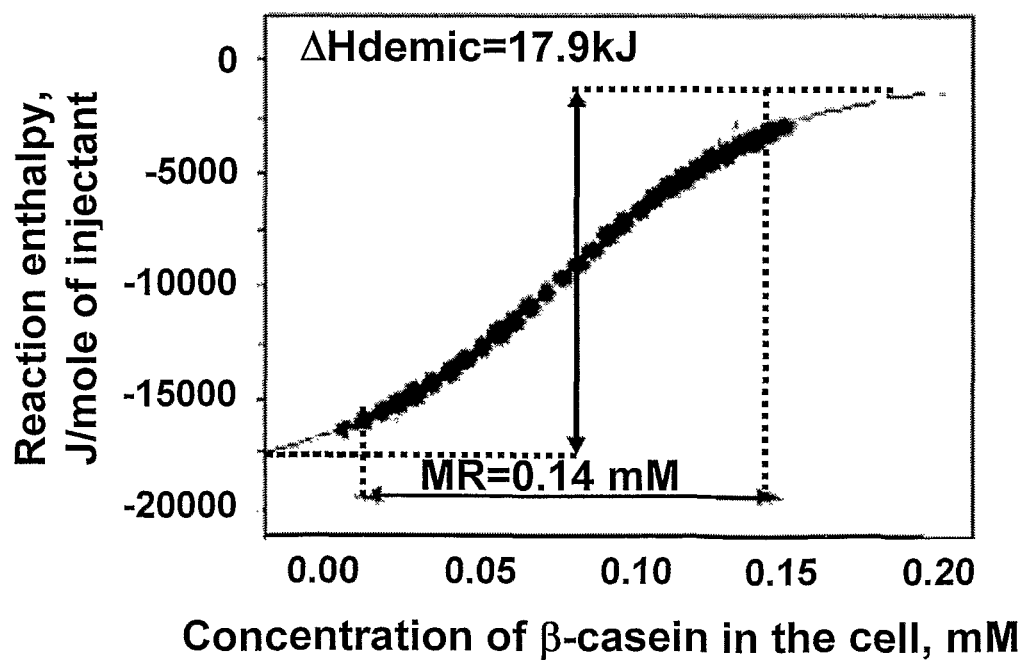
Figure 6C:
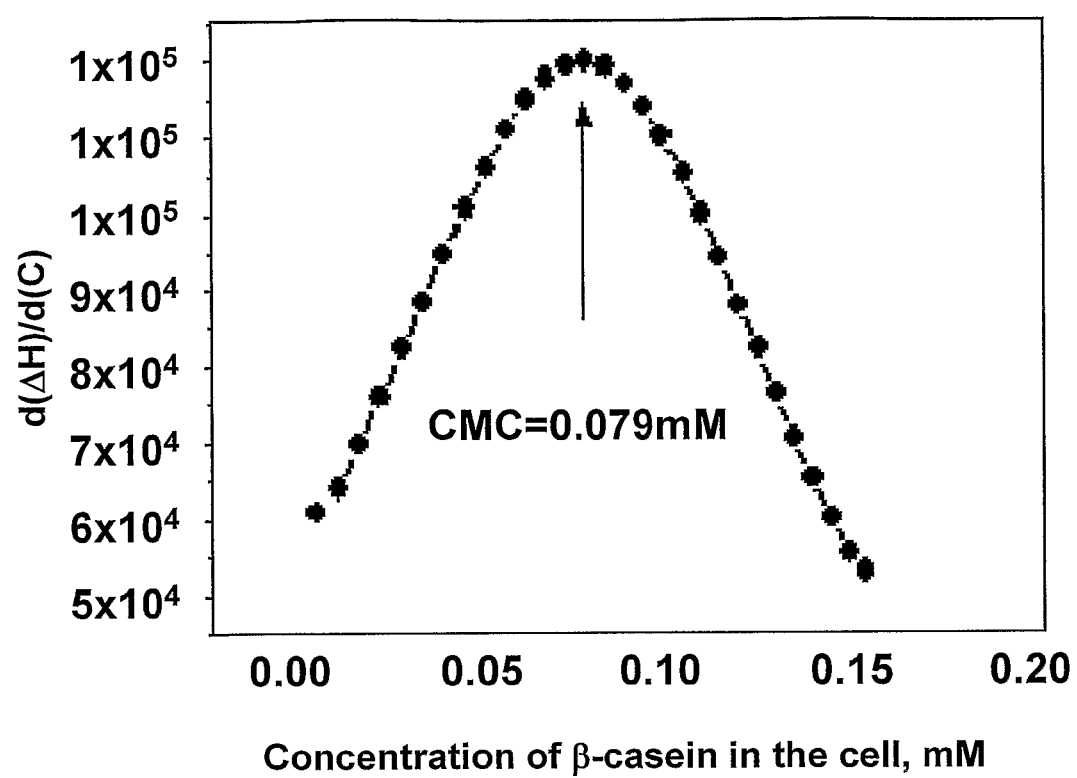

Characterization of the beta-casein micelles by ITC: beta-casein micellar solution was titrated into lactic acid buffer (pH 2.6) placed in the ITC cell, and the heat flow was measured as a function of time (FIG. 6A). Three factors contribute to the exothermic enthalpy changes observed at the initial injections: micelle dilution, demicellization, and dilution of individual beta-casein molecules. The enthalpy changes decrease in magnitude as more protein is added and the concentration in the ITC cell increases. Eventually, the concentration in the cell exceeds the CMC and only micelle dilution contributes to the heat flow. In FIG. 6B the heat of the reaction, obtained by integrating the peaks of the individual injections given in FIG. 6A, is plotted against the beta-casein concentration in the cell. A slow increase in the reaction enthalpy was observed, resulting in relative micellization cooperativity (MR) of 0.14 mM (FIG. 6B), which is more than twice than the value found at pH 7.0 and IS of 0.1. FIG. 6B also presents the heat of demicellization, ΔHdemic, which equals the enthalpy difference between the two asymptotes of the sigmoid fit of the experimental data (obtained by using the Origin software). It is shown that at 24° C. ΔHdemic is ~−17.9 kJ/mol, relatively small compared with the −40.53 kJ/mol found at pH 7.0 and IS of 0.1. The CMC, obtained from the beta-casein concentration at which the first derivative of the reaction heat displays a maximum, was determined to be 1.89 mg/mL (FIG. 6C) at pH 2.6. This value is approximately twice the CMC found at pH 7 and ionic strength 0.1. The small ΔHdemic, the high CMC, and the large MR indicate that the driving forces for micellization under acidic conditions are reduced compared with those at physiological pH and high IS.

Example 6

Figure 7:
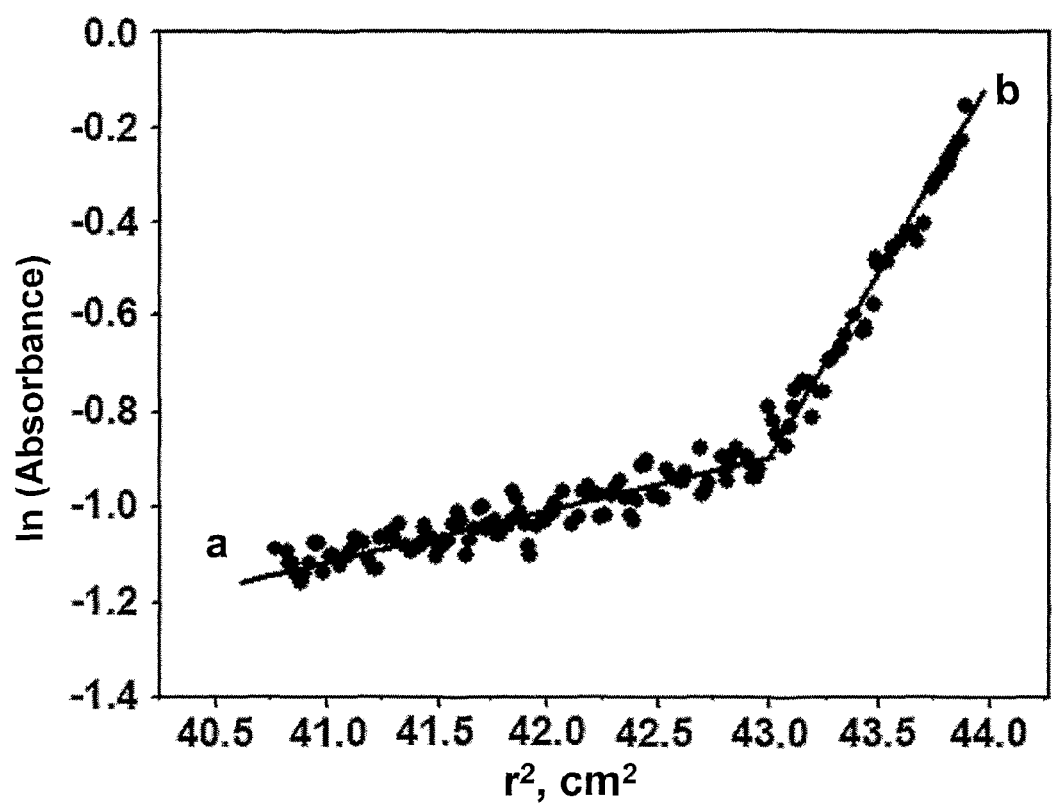
FIG. 7: Determination of β-casein aggregation number from the ultracentrifugation data at pH 2.6, protein concentration 5 mg/ml, ionic strength (IS) 0.002.

Characterization of the beta-casein micelles by Sedimentation Equilibrium: To determine the aggregation number of the micelles at pH 2.6, analytical ultracentrifugation experiments were conducted at various protein concentrations and at pH 7.0 and IS of 0.1. Sample data are plotted in FIG. 7. At concentrations lower than the CMC, determined by ITC to be 1.89 mg/mL (0.079 mM), a straight line was obtained. The aggregation numbers calculated from the slope of this line confirmed that the protein is monomeric at these concentrations. At concentrations higher than the CMC, two regions could be defined, indicating the presence of two protein populations: monomers at relatively short radii (i.e., in FIG. 7 at r<6.5 or r2<43) and assemblies at large radii. The micelles at pH 2.6 are characterized by a small aggregation number of 3 around the CMC and 6 at higher concentrations. In contrast, using the same technique we measured Nagg of 20 at pH 7.0 and ionic strength 0.1. Thus, compared with assembly at neutral pH, assembly at low pH is characterized by two special features: the micelles are flat and disk-like in shape, and they have a low molecular weight.

Example 7

Preparation of Beta-Casein Nano-Assemblies Loaded with Vitamin D at a pH Above the pI of Beta-Casein Preparation of empty beta-casein micelles above the pI: Weighted amounts of beta-casein were added to phosphate buffer solution (e.g. pH 7.0 phosphate buffer containing 5.65 mM $Na_2HPO_4$, and 3.05 mM $NaH_2PO_4$), pre-adjusted to the desired pH. Complete solubilization of protein was achieved within ~24 hr, at 4° C. A transparent solution is obtained.

Vitamin D2 (ergocalciferol—purchased from Sigma-Aldrich, Israel) was dissolved in absolute ethanol (Biolab Ltd., Israel) and poured slowly into beta-casein in buffer solutions while stirring, in order to obtain vitamin D:beta-casein molar ratios of: 1:1, 2:1, 4:1, 8:1, 16:1. Stock solutions of vitamin D in ethanol were prepared at such concentrations that while adding them to the protein or to buffer solution, the ethanol concentration would not exceed 5% of the total volume.

Figure 8:
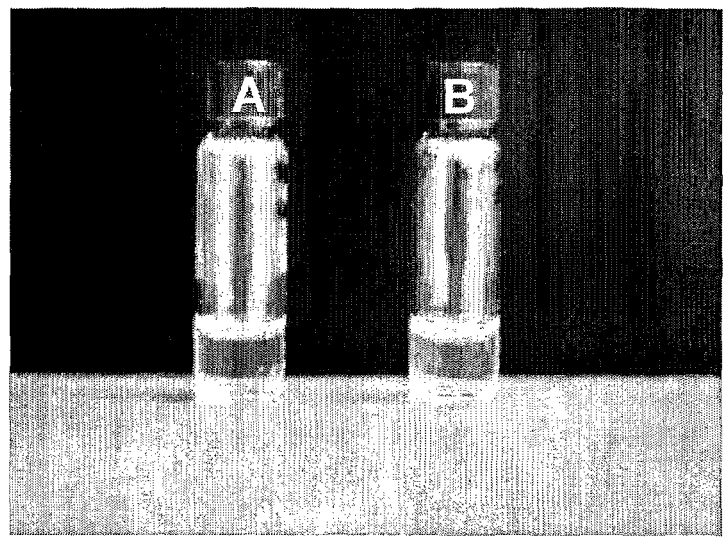
FIG. 8: (A) 0.1 wt % beta-casein in phosphate buffer (pH 7.02) loaded with vitamin D, at a 1:1 vitamin D:beta-casein molar ratio; (B) Vitamin D at same concentration and buffer as in A, without beta-casein.

The size of beta-casein micelles above the pI, at pH 7.0 and ionic strength of 0.1 ranges between 6 and 42 nm, with typical sizes of mainly 13-15 nm, and also 22-25 nm, depending on protein concentration. These dimensions were confirmed by SAXS measurements FIG. 8(A) shows a photograph of 0.1 wt % beta-casein in phosphate buffer (pH=7.02) loaded with vitamin D, at a 1:1 beta-casein:vitamin D molar ratio. FIG. 8(B) shows a solution of Vitamin D at the same concentration as in FIG. 1(A), in phosphate buffer (pH=7.02) without beta-casein. As can be clearly seen, a much clearer solution is obtained in the presence of beta-casein.

Figure 9:
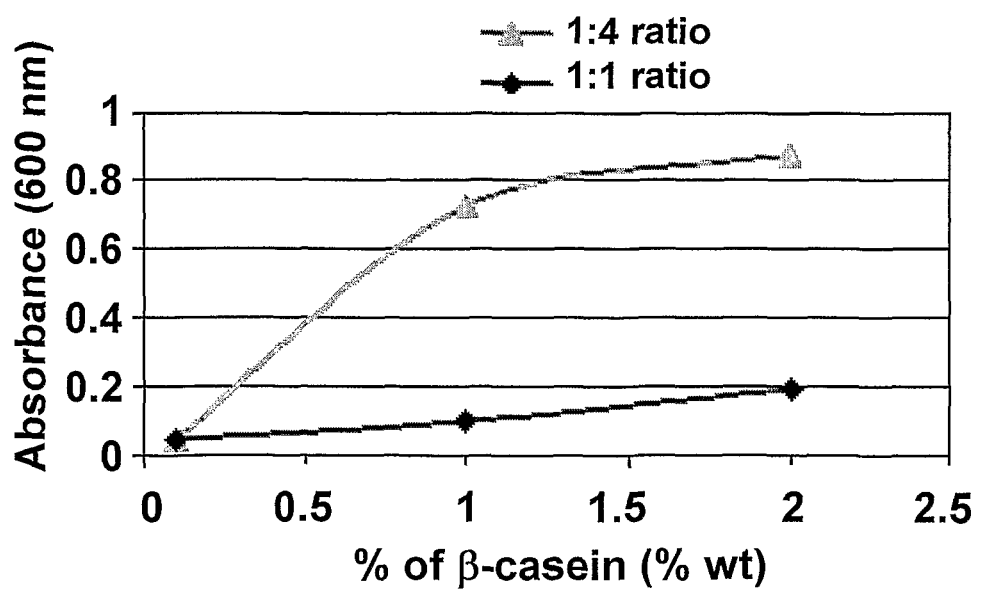
FIG. 9: shows a graph of turbidity measurements of vitamin D-loaded beta-casein assemblies (pH ~7), at beta-casein:vitamin D molar ratio of 1:1 and 1:4, according to an embodiment of the invention.

FIG. 9 shows a graph of turbidity measurements of vitamin D-loaded beta-casein assemblies (pH ~7), at beta-casein:vitamin D molar ratio of 1:1 (diamond) and 1:4 (triangle), according to an embodiment of the invention. It can be seen that at low loading:ratio (1:1) the solution turbidity remains fairly low at least up to 2 wt % of beta-casein. Increasing the loading to 1:4 beta-casein:vitamin D (molar) results in increased turbidity, which keeps rising with the beta-casein concentration.

Figure 10:
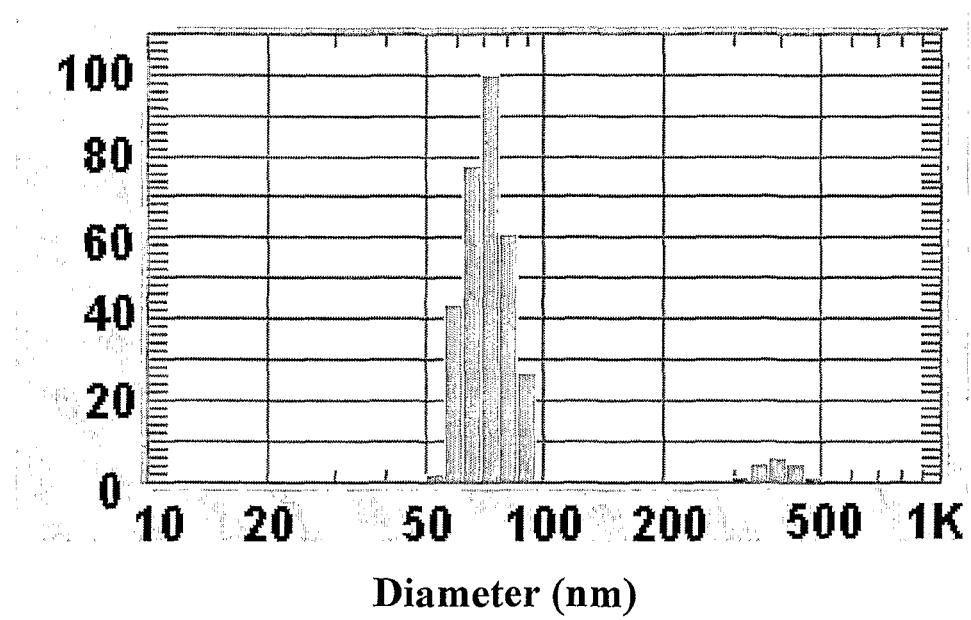
FIG. 10: A graphical presentation of the beta-casein micelle size distribution as determined by Dynamic light scattering at pH 7.0 with beta-casein:vitamin D molar ratio of 1:1.

Dynamic light scattering (DLS) data of beta-casein:vitamin D assemblies at pH 7.0 at a molar ratio of 1:1 (FIG. 10) shows the distribution of sizes of vitamin D loaded beta-casein micelles at pH 7.0. As can be seen, about 95% of the micelles are below 100 nm in size, which is in accordance with the very low turbidity results shown in FIG. 9.

Example 8

Preparation of Beta-Casein Nano-Assemblies Loaded with Vitamin D at a pH Below the pI of Beta-Casein Preparation of empty beta-casein micelles below the pI: Weighted amounts of beta-casein are added to lactic acid solution (~6 wt %), pre-adjusted to the desired pH. Complete solubilization of protein is achieved within ~36 hr, at 4° C. A transparent solution is obtained. The stock solution is diluted with lactic acid having the same pH, to the final concentration required. The solution can be stored at 4° C., for several weeks, depending on the pH and sterility. Sterile solutions are colloidally stable for months at both pH ranges-above and below the pI.

Vitamin D2 was dissolved in ethanol and poured slowly into pH 2.6 beta-casein solutions while stirring, in order to obtain vitamin D:beta-casein molar ratio of: 1:1, 2:1, 4:1, 8:1, 16:1. Stock solutions of vitamin D in ethanol were prepared in such concentrations that while adding them to the protein or to buffer solution, the ethanol concentration would not exceed 5% of the total volume.

Below the pI, the cross section of the beta-casein complexes is ~25 nm at 25° C. as observed by cryo-TEM. Their shape is typically flat and round (disk-like) and their aggregation number is between 6 and 10, depending on the conditions.

Figure 11:
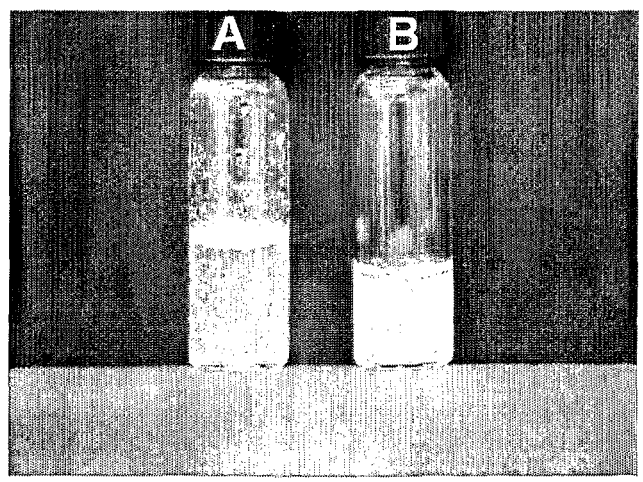
FIG. 11: Visual comparison at pH 2.5, of vitamin D dispersion (A) and vitamin D loaded beta-casein micelles (B).

Beta-casein in lactic acid, in the pH range of ~2.0-4.2 is transparent. Vitamin D does not solubilize in lactic acid as can be seen in FIG. 11(A). However adding vitamin D into the beta-casein micellar solution (2 wt % in lactic acid, pH 2.6) resulted with an opalescent, homogeneous solution in which vitamin D was solubilized as can be clearly seen in FIG. 11(B).

Figure 12:
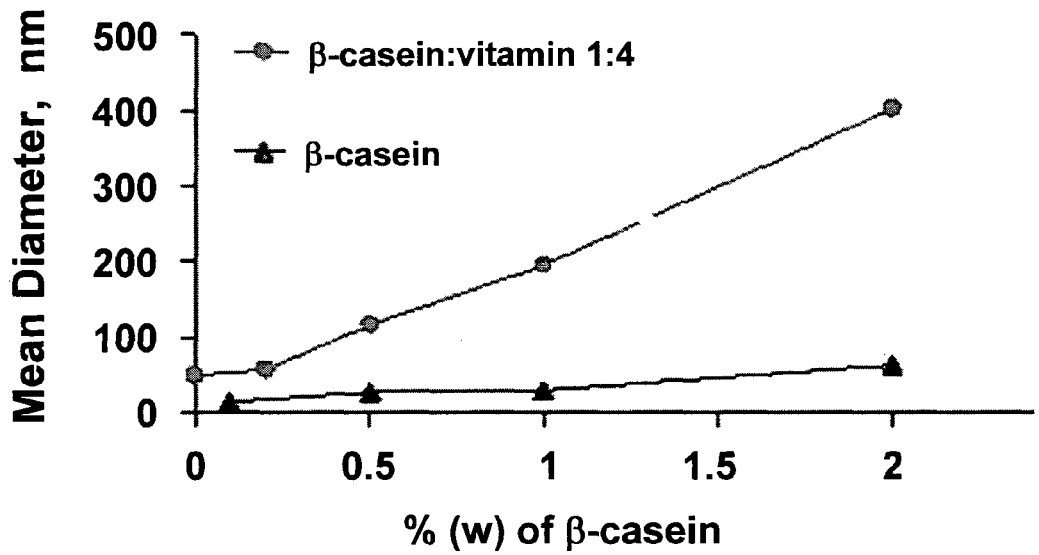
FIG. 12: The relation between the mean size of beta-casein assemblies, and the beta-casein concentration (at beta-casein:vitamin D molar ratio of 1:4 compared to pure beta-casein) at pH 2.6.

FIG. 12 shows the relation between the mean size of the assemblies, and the beta-casein concentration (at beta-casein:vitamin D molar ratio of 1:4 compared to pure beta-casein) at pH 2.6. The pure beta-casein micelles remain small, below 80 nm, consistent with the fact the solution remains transparent. For the vitamin-loaded assemblies, the figure clearly shows an increase in the mean size, with increasing the beta-casein concentration, from ~50 nm up to ~400 nm. This result is consistent with visual inspection showing the solution becomes opalescent. This data further shows that keeping the total concentration low can yield a transparent system of mixed beta-casein:vitamin assemblies (e.g., ≤0.25 wt %, 1:4 molar ratio).

Figure 13:
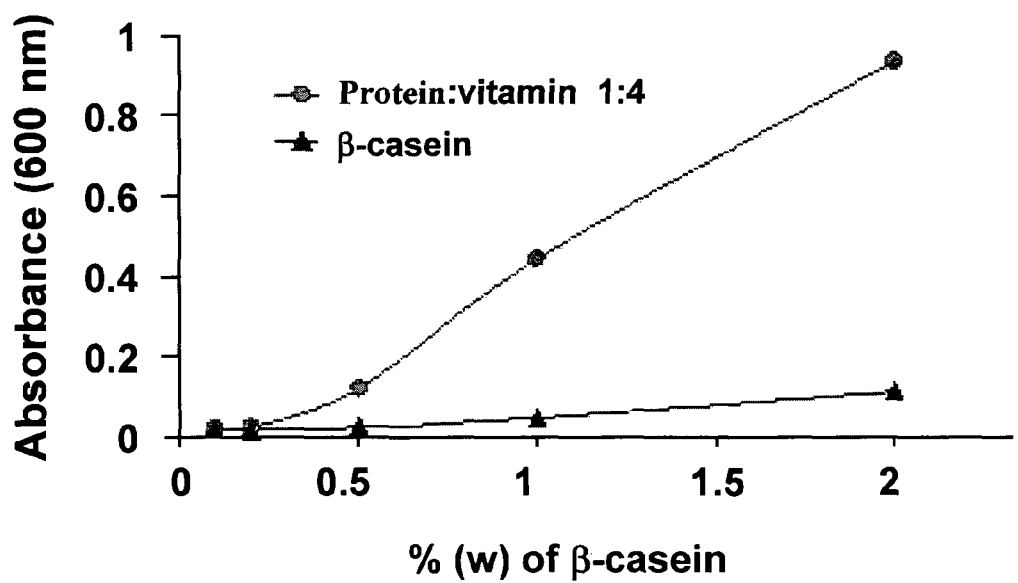
FIG. 13: Turbidity measurements of empty beta-casein assemblies, and the vitamin D-loaded beta-casein-assemblies at protein:vitamin D molar ratio of 1:4 (pH 2.6).

These results are further supported by turbidity studies (measured by the solution absorbance at 600 nm). For example, FIG. 13 shows turbidity measurements of the empty beta-casein assemblies, and the vitamin D-loaded nano-assemblies at protein:vitamin D molar ratio of 1:4 (pH 2.6). It can be seen that the turbidity of beta-casein micelles does not vary significantly up to at least 2 wt %, while that of the loaded assemblies continuously increases with protein concentration.

Figure 14A:
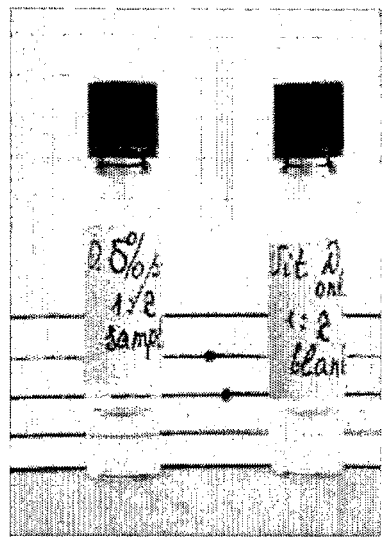
FIG. 14: shows a graphical presentation of the turbidity of the beta-casein assemblies at pH 7, according to embodiments of the invention; left vial—0.5% beta-casein, right vial—blank; (A) vitamin D:beta-casein ration of 2:1 and (B) vitamin D:beta-casein ratio of 4:1.
Figure 14B:
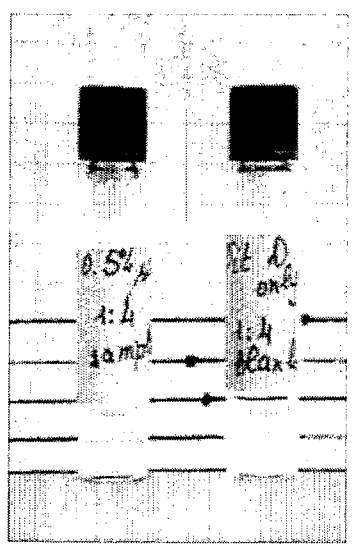

A visual comparison between the dissolution of vitamin D in the presence and absence of beta-casein at vitamin D:beta-casein ratio of 2:1 and 4:1 at pH 7, is shown in FIG. 14 (beta-casein concentration in both (a) and (b) was 0.5% by weight. It is clearly seen that samples containing beta-casein and vitamin D were less turbid than samples containing vitamin D only. It is also seen that increasing vitamin D:beta-casein ratio (thus increasing vitamin D concentration) leads, as expected, to increased turbidity of the solutions. The clarity (or turbidity) of a solution is a good indication for the colloidal stability of that solution; Thus, the better clarity of the beta-casein containing solutions the better the colloidal stability of these systems. It should be appreciated that the systems shown in FIG. 14 contain about 3000 times more vitamin per 100 ml than the current recommended daily allowance of vitamin D, reducing vitamin D concentration to the proper usage dose, will result with completely clear and stable beta-casein stabilized systems.

Figure 15A:
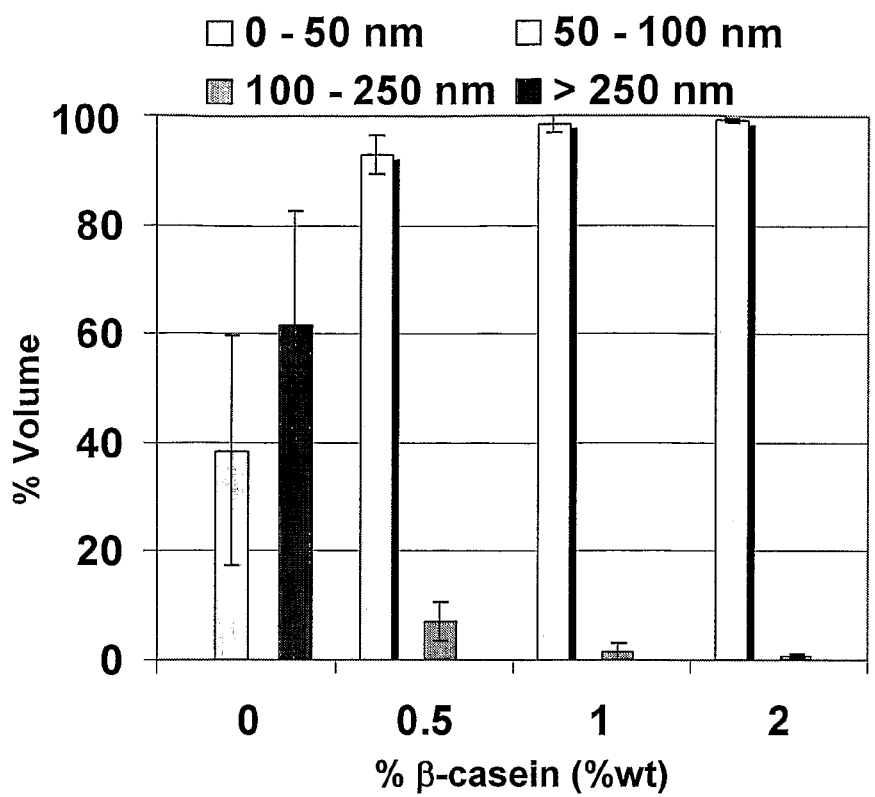
FIG. 15: Size distribution (A) and turbidity (B) of vitamin D loaded beta-casein micelles at pH 7.0, as a function of beta-casein concentration; Vitamin D concentration was 82.5 ug/ml.
Figure 15B:
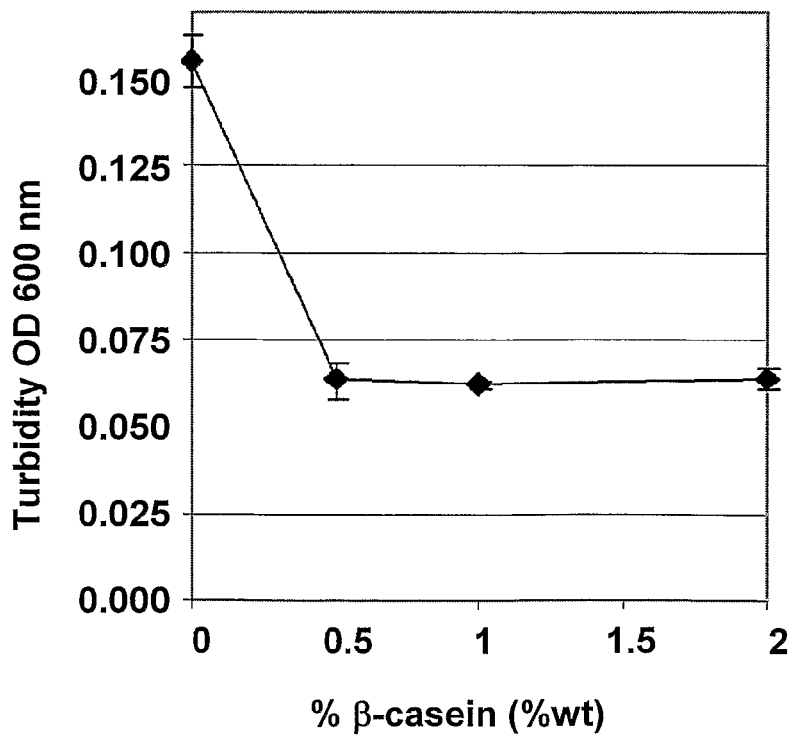
Figure 16A:
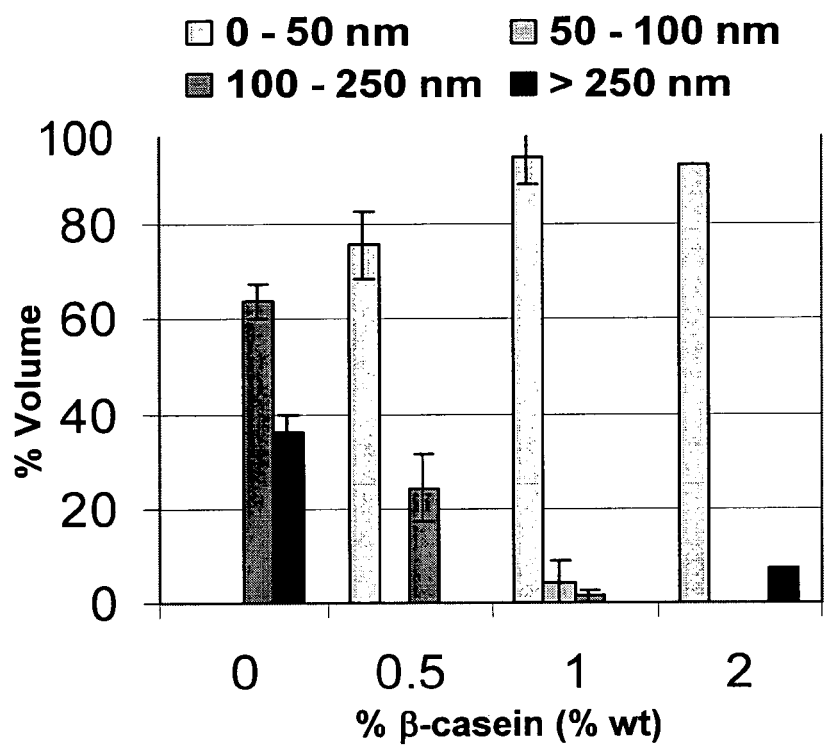
FIG. 16: Size distribution (A) and turbidity (B) of vitamin D loaded beta-casein micelles at pH 2.5, as a function of beta-casein concentration; Vitamin D concentration was 82.5 ug/ml.
Figure 16B:
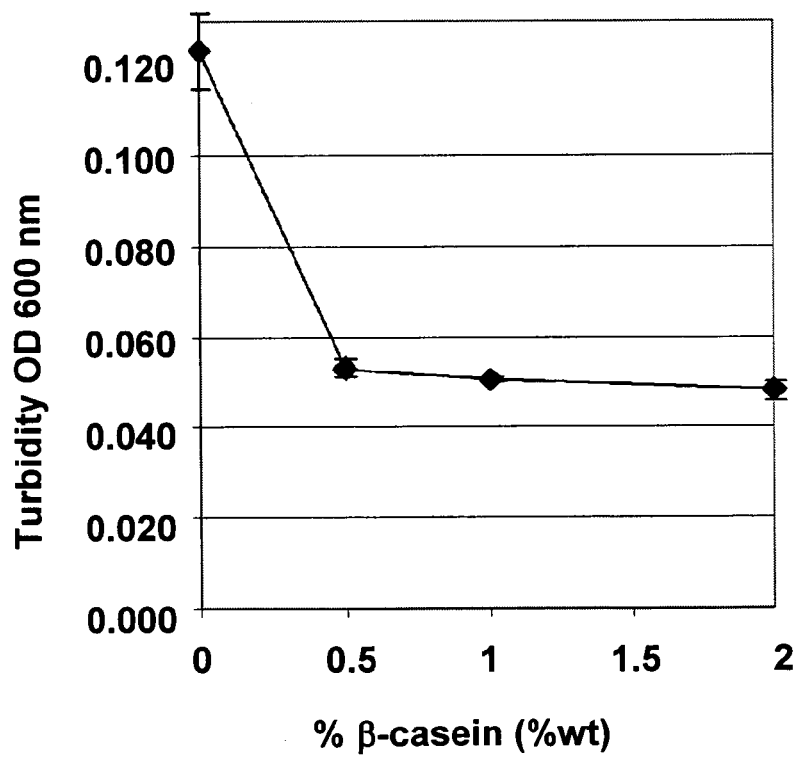

The particle size distribution and the turbidity of a vitamin D loaded beta-casein micellar solutions at pH 7.0 and pH 2.5 as a function of beta-casein concentration are shown in FIGS. 15 and 16 respectively. Vitamin D concentration in this experiment was kept constant (82.5 µg/ml; 0.2 mM) and the beta-casein concentration was raised gradually from 0 to 2% by weight (0 to 0.8 mM). As can be seen, adding beta-casein leads to decreasing particle size at both pH values, as determined by DLS, The mean particle diameter, as determined by DLS in this experiment, is about 25-30 nm. The corresponding turbidity results are in good accordance with the DLS results: in the absence of beta-casein there is sudden increase in turbidity value while in its presence, the turbidity value is much lower and almost constant in the range of protein concentrations used. This value is relatively low and the solutions looked transparent to the human eye.

Example 9

Figure 17A:
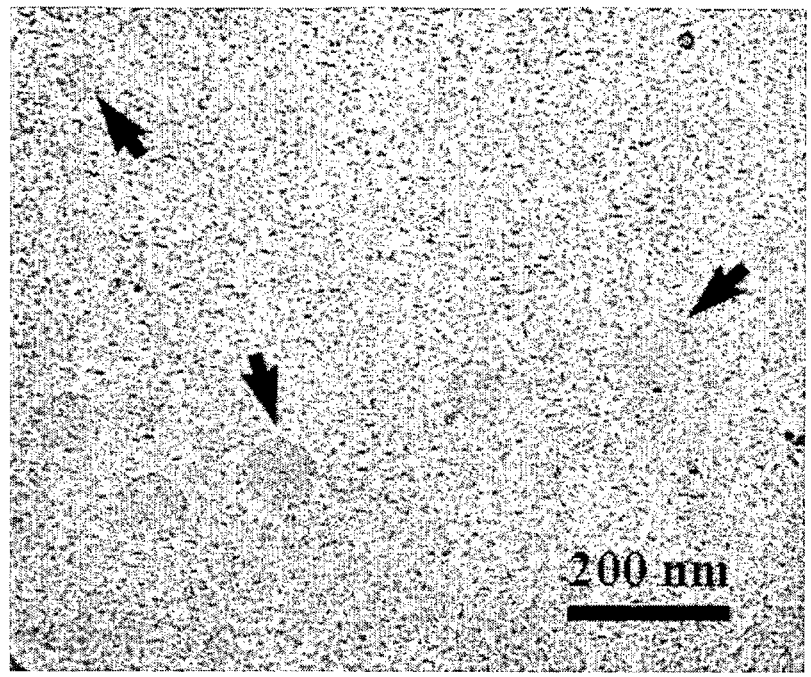
FIG. 17: Cryo-TEM images of beta-casein assemblies containing vitamin D, at pH 2.6, according to embodiments of the invention.
Figure 17B:
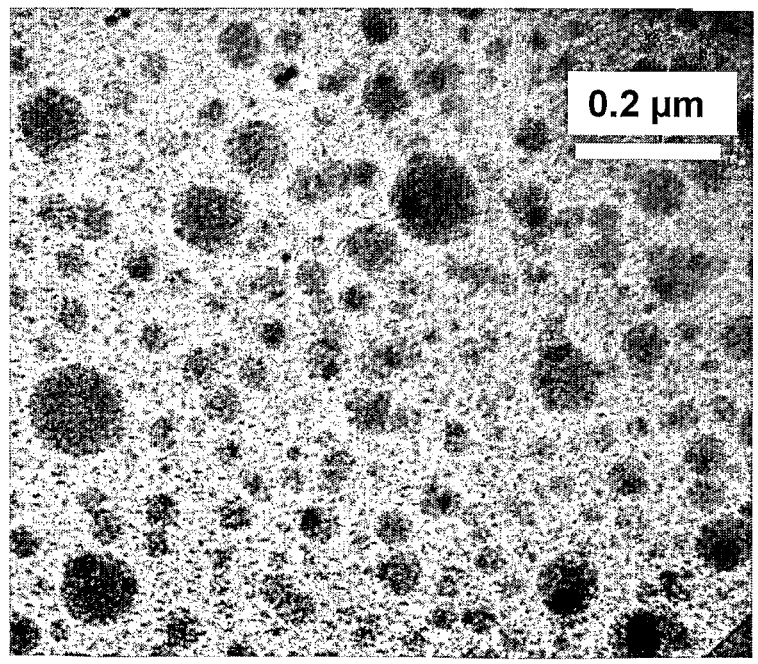

Characterization of the beta-casein:vitamin D assemblies formed at pH 2.6 by Cryo-TEM: Cryo-transmission electron microscopy was used to determine the shape and dimensions of the beta-casein and the mixed beta-casein:vitamin D assemblies at the nanoscale. Pure beta-casein micelles have a disk-like shape, their circular cross section is about 25 nm in diameter, and their width is about 3.5 nm. These assemblies appear in FIG. 17A as the small background structures. Upon solubilization of the vitamin D in beta-casein micellar solution, the micelles grow in the radial direction, to form large, flat, disc-shaped mixed assemblies with sizes ranging between ~25 nm to hundreds of nanometers in diameter, depending on the ratio between the components, and the total concentration of beta-casein (shown in FIG. 17A marked by arrows and in FIG. 17B).

Below the pI, vitamin D loaded assemblies are also disk-like in shape, their size can be tuned between 20 to 1000 nm to meet specific demands, e.g. by modifying the beta-casein: vitamin D ratio and concentrations.

Example 10

Vitamin D stability: In this part of the study the stability of vitamin D (heat, light and oxygen labile) in aqueous solutions was tested, with and without beta-casein. FIG. 18 presents two pictures of the same solutions, taken at a one week time difference. The right vial in FIG. 18a and FIG. 18b contains pure vitamin D in lactic acid buffer (pH 2.5), and is labeled "blank". The left vial contains vitamin D and beta-casein acidic solution (pH 2.5) at a molar ratio of 2:1 and with a beta-casein concentration of 0.5% wt. The aggregation of the vitamin D out of solution in the control system after a week is clearly observed by the white precipitation in FIG. 18b. Such precipitation was not observed in lactic acid buffer solutions containing beta-casein or in PBS solutions (both in the presence and in the absence of beta-casein).

We further tested the stability of vitamin D:beta-casein solutions in both acidic and neutral pH environments. The solutions prepared were left for a week at room temperature and the sampling was made once a day (in the first three days of the experiment) and once every two days (toward the end of the experiment). Vitamin D was extracted by n-hexane from each sample and its amount was analyzed using Reversed Phase HPLC. The amount of the vitamin left was compared to the amount extracted at time 0. The experiment was performed at two different pH values (pH 7 and pH 2.5). The results are presented in FIG. 19. It is clearly seen that the encapsulation of vitamin D in an aqueous solution of beta-casein stabilizes vitamin D. While vitamin D alone degrades rapidly leaving almost no trace after only two days, in the presence of beta-casein the degradation process is much slower and is not completed within the time of the experiment.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the spirit of the invention.

The invention clamed is:

1. A composition for the enrichment of food and/or beverage, the composition comprising beta-casein micelles loaded with an additive, wherein:
    the micelles are not held together by calcium-phosphate bridges and are selected from the group consisting of micelles comprising isolated beta-casein Prepared at a pH value at least one unit below the pI of beta-casein, wherein the isolated beta-casein is at least about 70% of the total casein and micelles comprising isolated beta-casein prepared at neutral pH, wherein the isolated beta-casein is at least about 70% of the total casein; and
    the micelles have an average diameter below about 100 nm.

2. The composition of claim 1 wherein the micelles have an average diameter of between about 25 nm and about 100 nm.

3. The composition of claim 1, wherein the composition is formed at a pH of between about 2 and about 4.2.

4. The composition of claim 1, wherein the additive is a hydrophobic nutraceutical.

5. The composition of claim 4, wherein the additive is vitamin-D or a derivative thereof.

6. The composition of claim 1 comprising up to about 2 wt % beta-casein.

7. The composition of claim 1 comprising 0.5 wt % beta-casein and a beta-casein: additive molar ratio of at least about 1:1.

8. The composition of claim 1 comprising a beta-casein: additive molar ratio of about 1:2 to 1:20.

9. A method for the preparation of a composition for the enrichment of food or beverage of claim 1, the method comprising: adding beta-casein to an aqueous solution selected from an acid solution having a pH at least one unit below the pI of beta-casein or a solution having a natural pH, wherein the beta casein is at least about 70% (w/w) of total casein;

mixing the solution at a temperature in the range of 1° C.-60° C. to obtain a solution of beta-casein micelles; adding an additive to the solution of beta-casein; and vigorously mixing the additive and solution of beta-casein until reaching a desired beta-casein: additive molar ratio.

10. The method of claim 9 wherein the buffer pH is in the range of about 2-about 4.2.

11. The method of claim 9 comprising mixing the solution at 4° C.

12. The method of claim 9 wherein the additive is a hydrophobic nutraceutical.

13. The method of claim 12 wherein the additive is vitamin-D or a derivative thereof.

14. The method of claim 9 wherein the desired beta-casein: additive molar ratio is between 1:1 to 1:20.

15. The method of claim 9 further comprising the step of adding the additive and beta-casein solution to a food or beverage to produce a functional food or beverage.

16. A functional food or beverage prepared by the method of claim 15.

17. The functional food or beverage of claim 16, wherein the food or beverage to be enriched is selected from the group consisting of a neutral or acid milk product, a low pH soft drink, a low-fat or non-fat food or beverage and a clear food or beverage.

18. A process for enrichment of a food or beverage comprising adding the composition of claim 1 to a food or beverage.

* * * * *